United States Patent
Woo et al.

(10) Patent No.: US 9,719,097 B2
(45) Date of Patent: *Aug. 1, 2017

(54) EXPRESSION VECTOR FOR CYANOBACTERIA

(71) Applicant: Korea Institute of Science and Technology, Seoul (KR)

(72) Inventors: Han Min Woo, Seoul (KR); Jun Won Chwa, Seoul (KR); Youngsoon Um, Seoul (KR); Gyeong Taek Gong, Seoul (KR); Yunje Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/860,373

(22) Filed: Sep. 21, 2015

(65) Prior Publication Data

US 2016/0168580 A1    Jun. 16, 2016

(30) Foreign Application Priority Data

Dec. 10, 2014 (KR) .................. 10-2014-0177540

(51) Int. Cl.
| | | |
|---|---|---|
| *C07H 21/02* | (2006.01) | |
| *C07H 21/04* | (2006.01) | |
| *A61K 48/00* | (2006.01) | |
| *C12N 15/74* | (2006.01) | |

(52) U.S. Cl.
CPC .................... *C12N 15/74* (2013.01)

(58) Field of Classification Search
CPC ............... C07H 21/04; A61K 39/00
USPC ......... 536/23.1, 23.7; 424/93.1, 93.2, 93.4
See application file for complete search history.

(56) References Cited

U.S. PATENT DOCUMENTS

2012/0259607 A1   10/2012 Hillson

FOREIGN PATENT DOCUMENTS

| KR | 10-2014-0042398 A | 4/2014 |
|---|---|---|
| WO | WO 2009/076559 A1 | 6/2009 |

OTHER PUBLICATIONS

Huang, Hsin-Ho, et al. "Design and characterization of molecular tools for a synthetic biology approach towards developing cyanobacterial biotechnology." Nucleic acids research (2010): 2577-2593.
"GeneArt® Genomic Cleavage Detection Kit", Invitrogen's User Guide, Catalog No. A24372, Publication No. MAN0009849, Jan. 9, 2014 (16 pages in English).
Invitrogen, User Guide. GeneArt® Synechococcus TOPO® Engineering Kits, Catalog Nos. A14261, A14265, Publication No. MAN0004977, Mar. 18, 2013 (33 pages in English).
GenBank Accession No. CP00010.1 (https://www.ncbi.nlm.nih.gov/nuccore/clipboard), Jan. 28, 2014 (456 pages).
Quan, Jiayuan, et al. "Circular polymerase extension cloning of complex gene libraries and pathways." PLoS one 4.7 (2009): e6441 (6 pages).
Huang, Hsin-Ho, et al. "Design and characterization of molecular tools for a synthetic biology approach toward developing cyanobacterial biotechnology." Nucleic acids research (2010): 2577-2593.
Lee, Taek Soon, et al. "BglBrick vectors and datasheets: a synthetic biology platform for gene expression." Journal of biological engineering 5.1 (2011): 1-14.
Ducat, Daniel C., et al. "Rerouting carbon flux to enhance photosynthetic productivity." Applied and environmental microbiology 78.8 (2012): 2660-2668.
Berla, Bertram M., et al. "Synthetic biology of cyanobacteria: unique challenges and opportunities." Frontiers in microbiology 4 (2013): (14 pages).
Taton, Arnaud, et al. "Broad-host-range vector system for synthetic biology and biotechnology in cyanobacteria." Nucleic acids research (2014): (16 pages).
"The SLIC, Gibson, CPEC and SLiCE assembly methods (and GeneArt® Seamless, In-Fusion® Cloning)" https://j5.jbei.org/j5manual/pages/22.html (2012): (5 pages).
"UTEX The Culture Collection of Algae" The University of Texas at Austin—http://www.utex.org/mediaDetail.aspx?mediaID=26 (1993): (1 page).

*Primary Examiner* — Rodney P Swartz
(74) *Attorney, Agent, or Firm* — NSIP Law

(57) ABSTRACT

The present disclosure discloses a vector that can be used for both cyanobacteria and *E. coli*, which contains, sequentially, a pUC replication origin as a replication origin; a spectinomycin-resistant gene as a selection marker; and a promoter selected from a group consisting of a trc promoter, a tetA promoter or a modified tetA promoter, a BAD promoter and a cbbL promoter. An industrially useful substance may be produced effectively using a host cell transformed with the vector. Also, the vector may be used to insert a variety of target genes through simple combination and, as a result, various vectors can be prepared effectively.

17 Claims, 27 Drawing Sheets

FIG. 8A 1. pSe1Bb1s-GFP sequence (5907bp)

GATAATCTCATGACCAAAATCCCTTAACGTGAGTTTTCGTTCCACTGAGCGTCAGACCCCGTAGA
AAAGATCAAAGGATCTTCTTGAGATCCTTTTTTTCTGCGCGTAATCTGCTGCTTGCAAACAAAAA
AACCACCGCTACCAGCGGTGGTTTGTTTGCCGGATCAAGAGCTACCAACTCTTTTTCCGAAGGT
AACTGGCTTCAGCAGAGCGCAGATACCAAATACTGTTCTTCTAGTGTAGCCGTAGTTAGGCCACC
ACTTCAAGAACTCTGTAGCACCGCCTACATACCTCGCTCTGCTAATCCTGTTACCAGTGGCTGCTG
CCAGTGGCGATAAGTCGTGTCTTACCGGGTTGGACTCAAGACGATAGTTACCGGATAAGGCGCA
GCGGTCGGGCTGAACGGGGGGTTCGTGCACACAGCCCAGCTTGGAGCGAACGACCTACACCGA
ACTGAGATACCTACAGCGTGAGCTATGAGAAAGCGCCACGCTTCCCGAAGGGAGAAAGGCGGA
CAGGTATCCGGTAAGCGGCAGGGTCGGAACAGGAGAGCGCACGAGGGAGCTTCCAGGGGGAA
ACGCCTGGTATCTTTATAGTCCTGTCGGGTTTCGCCACCTCTGACTTGAGCGTCGATTTTTGTGAT
GCTCGTCAGGGGGGCGGAGCCTATGGAAAAACGCCAGCAACGCGGCCTTTTACGGTTCCTGGCC
TTTTGCTGGCCTTTTGCTCACATGTGTGCTGGGCCCAATGCCTTCTCCAAGGGCGGCATTCCCCTG
ACTGTTGAAGGCGTTGCCAATATCAAGATTGCTGGGGAAGAACCGACCATCCACAACGCGATCG
AGCGGCTGCTTGGCAAAAACCGTAAGGAAATCGAGCAAATTGCCAAGGAGACCCTCGAAGGC
AACTTGCGTGGTGTTTTAGCCAGCCTCACGCCGGAGCAGATCAACGAGGACAAAATTGCCTTTG
CCAAAAGTCTGCTGGAAGAGGCGGAGGATGACCTTGAGCAGCTGGGTCAAGTCCTCGATACGC
TGCAAGTCCAGAACATTTCCGATGAGGTCGGTTATCTCTCGGCTAGTGGACGCAAGCAGCGGGC
TGATCTGCAGCGAGATGCCCGAATTGCTGAAGCCGATGCCCAGGCTGCCTCTGCGATCCAAACG
GCCGAAAATGACAAGATCACGGCCCTGCGTCGGATCGATCGCGATGTAGCGATCGCCCAAGCCG
AGGCCGAGCGCCGGATTCAGGATGCGTTGACGCGGCGCGAAGCGGTGGTGGCCGAAGCTGAA
GCGGACATTGCTACCGAAGTCGCTCGTAGCCAAGCAGAACTCCCTGTGCAGCAGGAGCGGATC
AAACAGGTGCAGCAGCAACTTCAAGCCGATGTGATCGCCCCAGCTGAGGCAGCTTGTAAACGG
GCGATCGCGGAAGCGCGGGGGGCCGCCGCCCGTATCGTCGAAGATGGAAAAGCTCAAGCGGA
AGGGACCCAACGGCTGGCGGAGGCTTGGCAGACCGCTGGTGCTAATGCCCGCGACATCTTCCTG
CTCCAGAAGTCTAGACCAGCCAGGACAGAAATGCCTCGACTTCGCTGCTACCCAAGGTTGCCGGGT
GACGCACACCGTGGAAACGGATGAAGGCACGAACCCAGTGGACATAAGCCTGTTCGGTTCGTAAGC
TGTAATGCAAGTAGCGTATGCGCTCACGCAACTGGTCCAGAACCTTGACCGAACGCAGCGGTGGT

FIG. 8B

AACGGCGCAGTGGCGGTTTTCATGGCTTGTTATGACTGTTTTTTTGGGGTACAGTCTATGCCTCG
GGCATCCAAGCAGCAAGCGCGTTACGCCGTGGGTCGATGTTTGATGTTATGGAGCAGCAACGAT
GTTACGCAGCAGGGCAGTCGCCCTAAAACAAAGTTAAACATTATGAGGGAAGCGGTGATCGCC
GAAGTATCGACTCAACTATCAGAGGTAGTTGGCGTCATCGAGCGCCATCTCGAACCGACGTTGCT
GGCCGTACATTTGTACGGCTCCGCAGTGGATGGCGGCCTGAAGCCACACAGTGATATTGATTTG
CTGGTTACGGTGACCGTAAGGCTTGATGAAACAACGCGGCGAGCTTTGATCAACGACCTTTTGG
AAACTTCGGCTTCCCCTGGAGAGAGCGAGATTCTCCGCGCTGTAGAAGTCACCATTGTTGTGCA
CGACGACATCATTCCGTGGCGTTATCCAGCTAAGCGCGAACTGCAATTTGGAGAATGGCAGCGC
AATGACATTCTTGCTGGTATCTTCGAGCCAGCCACGATCGACATTGATCTGGCTATCTTGCTGACA
AAAGCAAGAGAACATAGCGTTGCCTTGGTAGGTCCAGCGGCGGAGGAACTCTTTGATCCGGTT
CCTGAACAGGATCTATTTGAGGCGCTAAATGAAACCTTAACGCTATGGAACTCGCCGCCCGACT
GGGCTGGCGATGAGCGAAATGTAGTGCTTACGTTGTCCCGCATTTGGTACAGCGCAGTAACCGG
CAAAATCGCGCCGAAGGATGTCGCTGCCGACTGGGCAATGGAGCGCCTGCCGGCCCAGTATCAG
CCCGTCATACTTGAAGCTAGACAGGCTTATCTTGGACAAGAAGAAGATCGCTTGGCCTCGCGCG
CAGATCAGTTGGAAGAATTTGTCCACTACGTGAAAGGCGAGATCACCAAGGTAGTCGGCAAAT
AACCtcattttcgccagatatcgacgtcgacaccatcgaatggtgcaaaacctttcgcggtatggcatgatagcgcccggaaga
gagtcaattcaggtggtgaatgtgaaaccagtaacgttatacgatgtcgcagagtatgccggtgtctcttatcagaccgtt
tcccgcgtggtgaaccaggccagccacgtttctgcgaaaacgcgggaaaaagtggaagcggcgatggcggagctgaat
tacattcccaaccgcgtggcacaacaactggcgggcaaacagtcgttgctgattggcgttgccacctccagtctggccctg
cacgcgccgtcgcaaattgtcgcggcgattaaatctcgcgccgatcaactgggtgccagcgtggtgtgtcgatggtaga
acgaagcggcgtcgaagcctgtaaagcggcggtgcacaatcttctcgcgcaacgcgtcagtgggctgatcattaactatc
cgctggatgaccaggatgccattgctgtggaagctgcctgcactaatgttccggcgttatttcttgatgtctctgaccagaca
cccatcaacagtattattttctcccatgaagacggtacgcgactgggcgtggagcatctggtcgcattgggtcaccagcaa
atcgcgctgttagcgggcccattaagttctgtctcggcgcgtctgcgtctggctggctggcataaatatctcactcgcaatca
aattcagccgatagcggaacgggaaggcgactggagtgccatgtccggttttcaacaaaccatgcaaatgctgaatgag
ggcatcgttcccactgcgatgctggttgccaacgatcagatggcgctgggcgcaatgcgcgccattaccgagtccgggct
gcgcgttggtgcggatatctcggtagtgggatacgacgataccgaagacagctcatgttatatcccgccgttaaccaccat
caaacaggattttcgcctgctggggcaaaccagcgtggaccgcttgctgcaactctctcagggccaggcggtgaagggc

FIG. 8C aatcagctgttgcccgtctcactggtgaaaagaaaaaccaccctggcgcccaatacgcaaaccgcctctccccgcgcgttg
gccgattcattaatgcagctggcacgacaggtttcccgactggaaagcgggcagtgagcgcaacgcaattaatgtaagtta
gcgcgaattgatctggtttgacagcttatcatcgactgcacggtgcaccaatgcttctggcgtcaggcagccatcggaagctg
tggtatggctgtgcaggtcgtaaatcactgcataattcgtgtcgctcaaggcgcactcccgttctggataatgttttttgcgc
cgacatcataacggttctggcaaatattctgaaatgagctgttgacaattaatcatccggctcgtataatgtgtggaattgtg
agcggataacaatttcagaattcaaaagatcttttaagaaggagatatacatatgagtaaaggagaagaacttttcactgg
agttgtcccaattcttgttgaattagatggtgatgttaatgggcacaaattttctgtcagtggagagggtgaaggtgatgca
acatacggaaaacttacccttaaatttatttgcactactggaaaactacctgttccgtggccaacacttgtcactactttctctta
tggtgttcaatgcttttcccgttatccggatcacatgaaacggcatgacttttttcaagagtgccatgcccgaaggttatgtac
aggaacgcactatatctttcaaagatgacgggaactacaagacgcgtgctgaagtcaagtttgaaggtgatacccttgtta
atcgtatcgagttaaaaggtattgattttaaagaagatggaaacattctcggacacaaactggagtacaactataactcaca
caatgtatacatcacggcagacaaacaaaagaatggaatcaaagctaacttcaaaattcgccacaacattgaagatggctc
cgttcaactagcagaccattatcaacaaaatactccaattggcgatggccctgtccttttaccagacaaccattacctgtccac
acaatctgccctttcgaaagatcccaacgaaaagcgtgaccacatggtccttcttgagtttgtaactgctgctgggattacac
atggcatggatgagctctacaaataaggatccaaactcgagtaaggatctccaggcatcaaataaaacgaaaggctcagtcga
aagactgggcctttcgttttatctgttgtttgtcggtgaacgctctctactagagtcacactggctcaccttcgggtgggcctttctgc
gtttatacctagggcgttcggctgcggcgagcggtatcagctcactcaaaggcggtaatacgTCCCTGCTCGTCACGCT
TTCAGGCACCGTGCCAGATATCGACGTGGAGTCGATCACTGTGATTGGCGAAGGGGAAGGCAG
CGCTACCCAAATCGCTAGCTTGCTGGAGAAGCTGAAACAAACCACGGGCATTGATCTGGCGAA
ATCCCTACCGGGTCAATCCGACTCGCCCGCTGCGAAGTCCTAAGAGATAGCGATGTGACCGCGAT
CGCTTGTCAAGAATCCCAGTGATCCCGAACCATAGGAAGGCAAGCTCAATGCTTGCCTCGTCTTG
AGGACTATCTAGATGTCTGTGGAACGCACATTTATTGCCATCAAGCCCGATGGCGTTCAGCGGGG
TTTGGTCGGTACGATCATCGGCCGCTTTGAGCAAAAAGGCTTCAAACTGGTGGGCCTAAAGCAG
CTGAAGCCCAGTCGCGAGCTGGCCGAACAGCACTATGCTGTCCACCGCGAGCGCCCCTTCTTCA
ATGGCCTCGTCGAGTTCATCACCTCTGGGCCGATCGTGGCGATCGTCTTGGAAGGCGAAGGCGT
TGTGGCGGCTGCTCGCAAGTTGATCGGCGCTACCAATCCGCTGACGGCAGAACCGGGCACCATC
CGTGGTGATTTTGGTGTCAATATTGGCCGCAACATCATCCATGGCTCGGATGCAATCGAAACAGC
ACAACAGGAAATTGCTCTCTGGTTTAGCCCAGCAGAGCTAAGTGATTGGACCCCCACGATTCAA
CCCTGGCTGTACGAATAAGGTCTGCATTCCTTCAGAGAGACATTGCCATGCCC

FIG. 9A 2. pSe1Bb2s-GFP(5156bp)

GATAATCTCATGACCAAAATCCCTTAACGTGAGTTTTCGTTCCACTGAGCGTCAGACCCCGTAGA
AAAGATCAAAGGATCTTCTTGAGATCCTTTTTTTCTGCGCGTAATCTGCTGCTTGCAAACAA
AAAAACCACCGCTACCAGCGGTGGTTTGTTTGCCGGATCAAGAGCTACCAACTCTTTTTCCG
AAGGTAACTGGCTTCAGCAGAGCGCAGATACCAAATACTGTTCTTCTAGTGTAGCCGTAGTT
AGGCCACCACTTCAAGAACTCTGTAGCACCGCCTACATACCTCGCTCTGCTAATCCTGTTACC
AGTGGCTGCTGCCAGTGGCGATAAGTCGTGTCTTACCGGGTTGGACTCAAGACGATAGTTAC
CGGATAAGGCGCAGCGGTCGGGCTGAACGGGGGGTTCGTGCACACAGCCCAGCTTGGAGC
GAACGACCTACACCGAACTGAGATACCTACAGCGTGAGCTATGAGAAAGCGCCACGCTTCC
CGAAGGGAGAAAGGCGGACAGGTATCCGGTAAGCGGCAGGGTCGGAACAGGAGAGCGCA
CGAGGGAGCTTCCAGGGGGAAACGCCTGGTATCTTTATAGTCCTGTCGGGTTTCGCCACCTC
TGACTTGAGCGTCGATTTTTGTGATGCTCGTCAGGGGGCGGAGCCTATGGAAAAACGCCA
GCAACGCGGCCTTTTTACGGTTCCTGGCCTTTTGCTGGCCTTTTGCTCACATGTGTGCTGGGCCC
CAATGCCTTCTCCAAGGGCGGCATTCCCCTGACTGTTGAAGGCGTTGCCAATATCAAGATTG
CTGGGGAAGAACCGACCATCCACAACGCGATCGAGCGGCTGCTTGGCAAAAACCGTAAGG
AAATCGAGCAAATTGCCAAGGAGACCCTCGAAGGCAACTTGCGTGGTGTTTTAGCCAGCCT
CACGCCGGAGCAGATCAACGAGGACAAAATTGCCTTTGCCAAAAGTCTGCTGGAAGAGGC
GGAGGATGACCTTGAGCAGCTGGGTCAAGTCCTCGATACGCTGCAAGTCCAGAACATTTCC
GATGAGGTCGGTTATCTCTCGGCTAGTGGACGCAAGCAGCGGGCTGATCTGCAGCGAGATG
CCCGAATTGCTGAAGCCGATGCCCAGGCTGCCTCTGCGATCCAAACGGCCGAAAATGACAA
GATCACGGCCCTGCGTCGGATCGATCGCGATGTAGCGATCGCCCAAGCCGAGGCCGAGCGC
CGGATTCAGGATGCGTTGACGCGGCGCGAAGCGGTGGTGGCCGAAGCTGAAGCGGACATT
GCTACCGAAGTCGCTCGTAGCCAAGCAGAACTCCCTGTGCAGCAGGAGCGGATCAAACAG
GTGCAGCAGCAACTTCAAGCCGATGTGATCGCCCCAGCTGAGGCAGCTTGTAAACGGGCGA
TCGCGGAAGCGCGGGGGGCCGCCGCCCGTATCGTCGAAGATGGAAAAGCTCAAGCGGAAG
GGACCCAACGGCTGGCGGAGGCTTGGCAGACCGCTGGTGCTAATGCCCGCGACATCTTCCT
GCTCCAGAAGTCTAGACCAGCCAGGACAGAAATGCCTCGACTTCGCTGCTACCCAAGGTTGCC
GGGTGACGCACACCGTGGAAACGGATGAAGGCACGAACCCAGTGGACATAAGCCTGTTCGGTT

FIG. 9B

CGTAAGCTGTAATGCAAGTAGCGTATGCGCTCACGCAACTGGTCCAGAACCTTGACCGAACGC
AGCGGTGGTAACGGCGCAGTGGCGGTTTTCATGGCTTGTTATGACTGTTTTTTTGGGGTACA
GTCTATGCCTCGGGCATCCAAGCAGCAAGCGCGTTACGCCGTGGGTCGATGTTTGATGTTAT
GGAGCAGCAACGATGTTACGCAGCAGGGCAGTCGCCCTAAAACAAAGTTAAACATTATGA
GGGAAGCGGTGATCGCCGAAGTATCGACTCAACTATCAGAGGTAGTTGGCGTCATCGAGCG
CCATCTCGAACCGACGTTGCTGGCCGTACATTTGTACGGCTCCGCAGTGGATGGCGGCCTGA
AGCCACACAGTGATATTGATTTGCTGGTTACGGTGACCGTAAGGCTTGATGAAACAACGCG
GCGAGCTTTGATCAACGACCTTTTGGAAACTTCGGCTTCCCCTGGAGAGAGCGAGATTCTC
CGCGCTGTAGAAGTCACCATTGTTGTGCACGACGACATCATTCCGTGGCGTTATCCAGCTAA
GCGCGAACTGCAATTTGGAGAATGGCAGCGCAATGACATTCTTGCTGGTATCTTCGAGCCA
GCCACGATCGACATTGATCTGGCTATCTTGCTGACAAAAGCAAGAGAACATAGCGTTGCCTT
GGTAGGTCCAGCGGCGGAGGAACTCTTTGATCCGGTTCCTGAACAGGATCTATTTGAGGCG
CTAAATGAAACCTTAACGCTATGGAACTCGCCGCCCGACTGGGCTGGCGATGAGCGAAATG
TAGTGCTTACGTTGTCCCGCATTTGGTACAGCGCAGTAACCGGCAAAATCGCGCCGAAGGAT
GTCGCTGCCGACTGGGCAATGGAGCGCCTGCCGGCCCAGTATCAGCCCGTCATACTTGAAG
CTAGACAGGCTTATCTTGGACAAGAAGAAGATCGCTTGGCCTCGCGCGCAGATCAGTTGGA
AGAATTTGTCCACTACGTGAAAGGCGAGATCACCAAGGTAGTCGGCAAATAACCtcattttcgcc
agatatcgacgtcttaagacccactttcacatttaagttgttttctaatccgcatatgatcaattcaaggccgaataagaa
ggctggctctgcaccttggtgatcaaataattcgatagcttgtcgtaataatggcggcatactatcagtagtaggtgtt
tccctttcttctttagcgacttgatgctcttgatcttccaatacgcaacctaaagtaaaatgccccacagcgctgagtgca
tataatgcattctctagtgaaaaaccttgttggcataaaaaggctaattgattttcgagagtttcatactgttttttctgtag
gccgtgtacctaaatgtacttttgctccatcgcgatgacttagtaaagcacatctaaaactttagcgttattacgtaaaa
aatcttgccagctttccccttctaaagggcaaaagtgagtatggtgcctatctaacatctcaatggctaaggcgtcgag
caaagcccgcttatttttacatgccaatacaatgtaggctgctctacacctagcttctgggcgagtttacgggttgtta
aaccttcgattccgacctcattaagcagctctaatgcgctgttaatcactttacttttatctaatctagacatcattaattcc
taattttgttgacactctatcgttgatagagttattttaccactccctatcagtgatagagaaaagaattcaaaagatcttt
taagaaggagatatacatatgagtaaaggagaagaacttttcactggagttgtcccaattcttgttgaattagatggt
gatgttaatgggcacaaattttctgtcagtggagagggtgaaggtgatgcaacatacggaaaacttacccttaaattt
atttgcactactggaaaactacctgttccgtggccaacacttgtcactactttctcttatggtgttcaatgcttttcccgtta

FIG. 9C tccggatcacatgaaacggcatgacttttcaagagtgccatgcccgaaggttatgtacaggaacgcactatatctttc
aaagatgacgggaactacaagacgcgtgctgaagtcaagtttgaaggtgatacccttgttaatcgtatcgagttaaa
aggtattgattttaaagaagatggaaacattctcggacacaaactggagtacaactataactcacacaatgtatacatc
acggcagacaaacaaaagaatggaatcaaagctaacttcaaaattcgccacaacattgaagatggctccgttcaact
agcagaccattatcaacaaaatactccaattggcgatggccctgtccttttaccagacaaccattacctgtccacacaat
ctgcccttcgaaagatcccaacgaaagcgtgaccacatggtccttcttgagtttgtaactgctgctgggattacaca
tggcatggatgagctctacaaataaggatccaaactcgagtaaggatctccaggcatcaaataaaacgaaaggctcagt
cgaaagactgggcctttcgttttatctgttgtttgtcggtgaacgctctctactagagtcacactggctcaccttcgggtgggc
ctttctgcgtttatacctagggcgttcggctgcggcgagcggtatcagctcactcaaaggcggtaatacgTCCCTGCTC
GTCACGCTTTCAGGCACCGTGCCAGATATCGACGTGGAGTCGATCACTGTGATTGGCGAAG
GGGAAGGCAGCGCTACCCAAATCGCTAGCTTGCTGGAGAAGCTGAAACAAACCACGGGCA
TTGATCTGGCGAAATCCCTACCGGGTCAATCCGACTCGCCCGCTGCGAAGTCCTAAGAGATA
GCGATGTGACCGCGATCGCTTGTCAAGAATCCCAGTGATCCCGAACCATAGGAAGGCAAGC
TCAATGCTTGCCTCGTCTTGAGGACTATCTAGATGTCTGTGGAACGCACATTTATTGCCATCA
AGCCCGATGGCGTTCAGCGGGGTTTGGTCGGTACGATCATCGGCCGCTTTGAGCAAAAGG
CTTCAAACTGGTGGGCCTAAAGCAGCTGAAGCCCAGTCGCGAGCTGGCCGAACAGCACTAT
GCTGTCCACCGCGAGCGCCCCTTCTTCAATGGCCTCGTCGAGTTCATCACCTCTGGGCCGATC
GTGGCGATCGTCTTGGAAGGCGAAGGCGTTGTGGCGGCTGCTCGCAAGTTGATCGGCGCTA
CCAATCCGCTGACGGCAGAACCGGGCACCATCCGTGGTGATTTTGGTGTCAATATTGGCCGC
AACATCATCCATGGCTCGGATGCAATCGAAACAGCACAACAGGAAATTGCTCTCTGGTTTA
GCCCAGCAGAGCTAAGTGATTGGACCCCACGATTCAACCCTGGCTGTACGAATAAGGTCT
GCATTCCTTCAGAGAGACATTGCCATGCCC

FIG. 10A 3. pSe1Bb8s-GFP (5660bp)

GATAATCTCATGACCAAAATCCCTTAACGTGAGTTTTCGTTCCACTGAGCGTCAGAC**CCCGTAGA
AAAGATCAAAGGATCTTCTTGAGATCCTTTTTTTTCTGCGCGTAATCTGCTGCTTGCAAACAA
AAAAACCACCGCTACCAGCGGTGGTTTGTTTGCCGGATCAAGAGCTACCAACTCTTTTTCCG
AAGGTAACTGGCTTCAGCAGAGCGCAGATACCAAATACTGTTCTTCTAGTGTAGCCGTAGTT
AGGCCACCACTTCAAGAACTCTGTAGCACCGCCTACATACCTCGCTCTGCTAATCCTGTTACC
AGTGGCTGCTGCCAGTGGCGATAAGTCGTGTCTTACCGGGTTGGACTCAAGACGATAGTTAC
CGGATAAGGCGCAGCGGTCGGGCTGAACGGGGGGTTCGTGCACACAGCCCAGCTTGGAGC
GAACGACCTACACCGAACTGAGATACCTACAGCGTGAGCTATGAGAAAGCGCCACGCTTCC
CGAAGGGAGAAAGGCGGACAGGTATCCGGTAAGCGGCAGGGTCGGAACAGGAGAGCGCA
CGAGGGAGCTTCCAGGGGGAAACGCCTGGTATCTTTATAGTCCTGTCGGGTTTCGCCACCTC
TGACTTGAGCGTCGATTTTTGTGATGCTCGTCAGGGGGGCGGAGCCTATGGAAAA**ACGCCA
GCAACGCGGCCTTTTTACGGTTCCTGGCCTTTTGCTGGCCTTTTGCTCACATGTGTGCTGGGCCC
**CAATGCCTTCTCCAAGGGCGGCATTCCCCTGACTGTTGAAGGCGTTGCCAATATCAAGATTG
CTGGGGAAGAACCGACCATCCACAACGCGATCGAGCGGCTGCTTGGCAAAAACCGTAAGG
AAATCGAGCAAATTGCCAAGGAGACCCTCGAAGGCAACTTGCGTGGTGTTTTAGCCAGCCT
CACGCCGGAGCAGATCAACGAGGACAAAATTGCCTTTGCCAAAAGTCTGCTGGAAGAGGC
GGAGGATGACCTTGAGCAGCTGGGTCAAGTCCTCGATACGCTGCAAGTCCAGAACATTTCC
GATGAGGTCGGTTATCTCTCGGCTAGTGGACGCAAGCAGCGGGCTGATCTGCAGCGAGATG
CCCGAATTGCTGAAGCCGATGCCCAGGCTGCCTCTGCGATCCAAACGGCCGAAAATGACAA
GATCACGGCCCTGCGTCGGATCGATCGCGATGTAGCGATCGCCCAAGCCGAGGCCGAGCGC
CGGATTCAGGATGCGTTGACGCGGCGCGAAGCGGTGGTGGCCGAAGCTGAAGCGGACATT
GCTACCGAAGTCGCTCGTAGCCAAGCAGAACTCCCTGTGCAGCAGGAGCGGATCAAACAG
GTGCAGCAGCAACTTCAAGCCGATGTGATCGCCCCAGCTGAGGCAGCTTGTAAACGGGCGA
TCGCGGAAGCGCGGGGGCCGCCGCCCGTATCGTCGAAGATGGAAAAGCTCAAGCGGAAG
GGACCCAACGGCTGGCGGAGGCTTGGCAGACCGCTGGTGCTAATGCCCGCGACATCTTCCT
GCTCCAGAAG**TCTAGACCAGCCAGGACAGAAATGCCTCGACTTCGCTGCTACCCAAGGTTGCC
GGGTGACGCACACCGTGGAAACGGATGAAGGCACGAACCCAGTGGACATAAGCCTGTTCGGTT

FIG. 10B

CGTAAGCTGTAATGCAAGTAGCGTATGCGCTCACGCAACTGGTCCAGAACCTTGACCGAACGC
AGCGGTGGTAACGGCGCAGTGGCGGTTTTCATGGCTTGTTATGACTGTTTTTTTGGGGTACA
GTCTATGCCTCGGGCATCCAAGCAGCAAGCGCGTTACGCCGTGGGTCGATGTTTGATGTTAT
GGAGCAGCAACGATGTTACGCAGCAGGGCAGTCGCCCTAAAACAAAGTTAAACATTATGA
GGGAAGCGGTGATCGCCGAAGTATCGACTCAACTATCAGAGGTAGTTGGCGTCATCGAGCG
CCATCTCGAACCGACGTTGCTGGCCGTACATTTGTACGGCTCCGCAGTGGATGGCGGCCTGA
AGCCACACAGTGATATTGATTTGCTGGTTACGGTGACCGTAAGGCTTGATGAAACAACGCG
GCGAGCTTTGATCAACGACCTTTTGGAAACTTCGGCTTCCCCTGGAGAGAGCGAGATTCTC
CGCGCTGTAGAAGTCACCATTGTTGTGCACGACGACATCATTCCGTGGCGTTATCCAGCTAA
GCGCGAACTGCAATTTGGAGAATGGCAGCGCAATGACATTCTTGCTGGTATCTTCGAGCCA
GCCACGATCGACATTGATCTGGCTATCTTGCTGACAAAAGCAAGAGAACATAGCGTTGCCTT
GGTAGGTCCAGCGGCGGAGGAACTCTTTGATCCGGTTCCTGAACAGGATCTATTTGAGGCG
CTAAATGAAACCTTAACGCTATGGAACTCGCCGCCCGACTGGGCTGGCGATGAGCGAAATG
TAGTGCTTACGTTGTCCCGCATTTGGTACAGCGCAGTAACCGGCAAAATCGCGCCGAAGGAT
GTCGCTGCCGACTGGGCAATGGAGCGCCTGCCGGCCCAGTATCAGCCCGTCATACTTGAAG
CTAGACAGGCTTATCTTGGACAAGAAGAAGATCGCTTGGCCTCGCGCGCAGATCAGTTGGA
AGAATTTGTCCACTACGTGAAAGGCGAGATCACCAAGGTAGTCGGCAAATAACCtcattttcgcc
agatatcgacgtcttatgacaacttgacggctacatcattcacttttcttcacaaccggcacggaactcgctcgggctg
gccccggtgcattttttaaatacccgcgagaaatagagttgatcgtcaaaaccaacattgcgaccgacggtggcgat
aggcatccgggtggtgctcaaaagcagcttcgcctggctgatacgttggtcctcgcgccagcttaagacgctaatcc
ctaactgctggcggaaaagatgtgacagacgcgacggcgacaagcaaacatgctgtgcgacgctggcgatatcaa
aattgctgtctgccaggtgatcgctgatgtactgacaagcctcgcgtacccgattatccatcggtggatggagcgact
cgttaatcgcttccatgcgccgcagtaacaattgctcaagcagatttatcgccagcagctccgaatagcgcccttcccct
tgcccggcgttaatgatttgcccaaacaggtcgctgaaatgcggctggtgcgcttcatccgggcgaaagaacccgt
attggcaaatattgacggccagttaagccattcatgccagtaggcgcgcggacgaaagtaaacccactggtgatacc
attcgcgagcctccggatgacgaccgtagtgatgaatctctcctggcgggaacagcaaaatatcacccggtcggcaa
acaaattctcgtccctgattttcaccaccccctgaccgcgaatggtgagattgagaatataacctttcattcccagcgg
tcggtcgataaaaaaatcgagataaccgttggcctcaatcggcgttaaacccgccaccagatgggcattaaacgagt
atcccggcagcaggggatcattttgcgcttcagccatactttcatactcccgccattcagagaagaaaccaattgtccata

FIG. 10C ttgcatcagacattgccgtcactgcgtcttttactggctcttctcgctaaccaaaccggtaacccccgcttattaaaagcattctgt
aacaaagcgggaccaaagccatgacaaaaacgcgtaacaaaagtgtctataatcacggcagaaaagtccacattgattatt
tgcacggcgtcacactttgctatgccatagcattttttatccataagattagcggattctacct<u>gacgcttttatcgcaactctct</u>
<u>actgtttctccatacccgttttttt</u>gggaattcaaaagatct<u>tttaagaaggagatatacatatgagtaaaggagaagaact</u>
<u>tttcactggagttgtcccaattcttgttgaattagatggtgatgttaatgggcacaaattttctgtcagtggagagggt</u>
<u>gaaggtgatgcaacatacggaaaacttacccttaaatttatttgcactactggaaaactacctgttccgtggccaacac</u>
<u>ttgtcactactttctcttatggtgttcaatgcttttcccgttatccggatcacatgaaacggcatgacttttttcaagagtgc</u>
<u>catgcccgaaggttatgtacaggaacgcactatatctttcaaagatgacgggaactacaagacgcgtgctgaagtca</u>
<u>agtttgaaggtgataccccttgttaatcgtatcgagttaaaaggtattgattttaaagaagatggaaacattctcggaca</u>
<u>caaactggagtacaactataactcacacaatgtatacatcacggcagacaaacaaaagaatggaatcaaagctaactt</u>
<u>caaaattcgccacaacattgaagatggctccgttcaactagcagaccattatcaacaaaatactccaattggcgatggc</u>
<u>cctgtccttttaccagacaaccattacctgtccacacaatctgccctttcgaaagatcccaacgaaaagcgtgaccacat</u>
<u>ggtccttcttgagtttgtaactgctgctgggattacacatggcatggatgagctctacaaataag</u>gatccaaactcgag
taaggatctccaggcatcaaataaaacgaaaggctcagtcgaaagactgggcctttcgttttatctgttgtttgtcggtgaac
gctctctactagagtcacactggctcaccttgggtgggcctttctgcgtttatacctagggcgttcggctgcggcgagcggt
atcagctcactcaaaggcggtaatacg<u>TCCCTGCTCGTCACGCTTTCAGGCACCGTGCCAGATATCGAC</u>
<u>GTGGAGTCGATCACTGTGATTGGCGAAGGGGAAGGCAGCGCTACCCAAATCGCTAGCTTGC</u>
<u>TGGAGAAGCTGAAACAAACCACGGGCATTGATCTGGCGAAATCCCTACCGGGTCAATCCGA</u>
<u>CTCGCCCGCTGCGAAGTCCTAAGAGATAGCGATGTGACCGCGATCGCTTGTCAAGAATCCCA</u>
<u>GTGATCCCGAACCATAGGAAGGCAAGCTCAATGCTTGCCTCGTCTTGAGGACTATCTAGATG</u>
<u>TCTGTGGAACGCACATTTATTGCCATCAAGCCCGATGGCGTTCAGCGGGGTTTGGTCGGTAC</u>
<u>GATCATCGGCCGCTTTGAGCAAAAAGGCTTCAAACTGGTGGGCCTAAAGCAGCTGAAGCC</u>
<u>CAGTCGCGAGCTGGCCGAACAGCACTATGCTGTCCACCGCGAGCGCCCCTTCTTCAATGGCC</u>
<u>TCGTCGAGTTCATCACCTCTGGGCCGATCGTGGCGATCGTCTTGGAAGGCGAAGGCGTTGTG</u>
<u>GCGGCTGCTCGCAAGTTGATCGGCGCTACCAATCCGCTGACGGCAGAACCGGGCACCATCC</u>
<u>GTGGTGATTTTGGTGTCAATATTGGCCGCAACATCATCCATGGCTCGGATGCAATCGAAACA</u>
<u>GCACAACAGGAAATTGCTCTCTGGTTTAGCCCAGCAGAGCTAAGTGATTGGACCCCCACGA</u>
<u>TTCAACCCTGGCTGTACGAATAAGGTCTGCATTCCTTCAGAGAGACATTGCCATGCCC</u>

FIG. 11A 4. pSe1Bb<sub>cbbl</sub>S-GFP(4670bp)

GATAATCTCATGACCAAAATCCCTTAACGTGAGTTTTCGTTCCACTGAGCGTCAGAC<u>CCCGTAGA</u>
<u>AAAGATCAAAGGATCTTCTTGAGATCCTTTTTTTCTGCGCGTAATCTGCTGCTTGCAAACAA</u>
<u>AAAAACCACCGCTACCAGCGGTGGTTTGTTTGCCGGATCAAGAGCTACCAACTCTTTTTCCG</u>
<u>AAGGTAACTGGCTTCAGCAGAGCGCAGATACCAAATACTGTTCTTCTAGTGTAGCCGTAGTT</u>
<u>AGGCCACCACTTCAAGAACTCTGTAGCACCGCCTACATACCTCGCTCTGCTAATCCTGTTACC</u>
<u>AGTGGCTGCTGCCAGTGGCGATAAGTCGTGTCTTACCGGGTTGGACTCAAGACGATAGTTAC</u>
<u>CGGATAAGGCGCAGCGGTCGGGCTGAACGGGGGGTTCGTGCACACAGCCCAGCTTGGAGC</u>
<u>GAACGACCTACACCGAACTGAGATACCTACAGCGTGAGCTATGAGAAAGCGCCACGCTTCC</u>
<u>CGAAGGGAGAAAGGCGGACAGGTATCCGGTAAGCGGCAGGGTCGGAACAGGAGAGCGCA</u>
<u>CGAGGGAGCTTCCAGGGGGAAACGCCTGGTATCTTTATAGTCCTGTCGGGTTTCGCCACCTC</u>
<u>TGACTTGAGCGTCGATTTTTGTGATGCTCGTCAGGGGGGCGGAGCCTATGGAAAA</u>ACGCCA
GCAACGCGGCCTTTTTACGGTTCCTGGCCTTTTGCTGGCCTTTTGCTCACATGTGTGCTGGGCCC
<u>CAATGCCTTCTCCAAGGGCGGCATTCCCCTGACTGTTGAAGGCGTTGCCAATATCAAGATTG</u>
<u>CTGGGGAAGAACCGACCATCCACAACGCGATCGAGCGGCTGCTTGGCAAAAACCGTAAGG</u>
<u>AAATCGAGCAAATTGCCAAGGAGACCCTCGAAGGCAACTTGCGTGGTGTTTTAGCCAGCCT</u>
<u>CACGCCGGAGCAGATCAACGAGGACAAAATTGCCTTTGCCAAAAGTCTGCTGGAAGAGGC</u>
<u>GGAGGATGACCTTGAGCAGCTGGGTCAAGTCCTCGATACGCTGCAAGTCCAGAACATTTCC</u>
<u>GATGAGGTCGGTTATCTCTCGGCTAGTGGACGCAAGCAGCGGGCTGATCTGCAGCGAGATG</u>
<u>CCCGAATTGCTGAAGCCGATGCCCAGGCTGCCTCTGCGATCCAAACGGCCGAAAATGACAA</u>
<u>GATCACGGCCCTGCGTCGGATCGATCGCGATGTAGCGATCGCCCAAGCCGAGGCCGAGCGC</u>
<u>CGGATTCAGGATGCGTTGACGCGGCGCAAGCGGTGGTGGCCGAAGCTGAAGCGGACATT</u>
<u>GCTACCGAAGTCGCTCGTAGCCAAGCAGAACTCCCTGTGCAGCAGGAGCGGATCAAACAG</u>
<u>GTGCAGCAGCAACTTCAAGCCGATGTGATCGCCCCAGCTGAGGCAGCTTGTAAACGGGCGA</u>
<u>TCGCGGAAGCGCGGGGGCCGCCGCCCGTATCGTCGAAGATGGAAAAGCTCAAGCGGAAG</u>
<u>GGACCCAACGGCTGGCGGAGGCTTGGCAGACCGCTGGTGCTAATGCCCGCGACATCTTCCT</u>
<u>GCTCCAGAAG</u>TCTAGACCAGCCAGGACAGAAATGCCTCGACTTCGCTGCTACCCAAGGTTGCC
GGGTGACGCACACCGTGGAAACGGATGAAGGCACGAACCCAGTGGACATAAGCCTGTTCGGTT

FIG. 11B

CGTAAGCTGTAATGCAAGTAGCGTATGCGCTCACGCAACTGGTCCAGAACCTTGACCGAACGC
AGCGGTGGTAACGGCGCAGTGGCGGTTTTCATGGCTTGTTATGACTGTTTTTTTGGGGTACA
GTCTATGCCTCGGGCATCCAAGCAGCAAGCGCGTTACGCCGTGGGTCGATGTTTGATGTTAT
GGAGCAGCAACGATGTTACGCAGCAGGGCAGTCGCCCTAAAACAAAGTTAAACATTATGA
GGGAAGCGGTGATCGCCGAAGTATCGACTCAACTATCAGAGGTAGTTGGCGTCATCGAGCG
CCATCTCGAACCGACGTTGCTGGCCGTACATTTGTACGGCTCCGCAGTGGATGGCGGCCTGA
AGCCACACAGTGATATTGATTTGCTGGTTACGGTGACCGTAAGGCTTGATGAAACAACGCG
GCGAGCTTTGATCAACGACCTTTTGGAAACTTCGGCTTCCCCTGGAGAGAGCGAGATTCTC
CGCGCTGTAGAAGTCACCATTGTTGTGCACGACGACATCATTCCGTGGCGTTATCCAGCTAA
GCGCGAACTGCAATTTGGAGAATGGCAGCGCAATGACATTCTTGCTGGTATCTTCGAGCCA
GCCACGATCGACATTGATCTGGCTATCTTGCTGACAAAAGCAAGAGAACATAGCGTTGCCTT
GGTAGGTCCAGCGGCGGAGGAACTCTTTGATCCGGTTCCTGAACAGGATCTATTTGAGGCG
CTAAATGAAACCTTAACGCTATGGAACTCGCCGCCCGACTGGGCTGGCGATGAGCGAAATG
TAGTGCTTACGTTGTCCCGCATTTGGTACAGCGCAGTAACCGGCAAAATCGCGCCGAAGGAT
GTCGCTGCCGACTGGGCAATGGAGCGCCTGCCGGCCCAGTATCAGCCCGTCATACTTGAAG
CTAGACAGGCTTATCTTGGACAAGAAGAAGATCGCTTGGCCTCGCGCGCAGATCAGTTGGA
AGAATTTGTCCACTACGTGAAAGGCGAGATCACCAAGGTAGTCGGCAAATAACCtcattttcgcc
agatatcgacgtcgacATCTCGCTTCTGGGCTTCAATAAATGGTTCCGATTGATGATAGGTTGATTC
ATGAGGAATCTAAGGCTTAATTCTCCACAAAAGAATTAAGCGTCCGTCGCAACGGAATGCTC
CGCTGGACTTGCGCTGTGGGACTGCAGCTTTACAGGCTCCCCCTGCCAGAAATCCTGAATCG
TCGAGCATATCTGACATATCTCTAGGGAGAGACGACgaattcaaaagatctttaagaaggagatataca
tatgagtaaaggagaagaacttttcactggagttgtcccaattcttgttgaattagatggtgatgttaatgggcacaaa
ttttctgtcagtggagagggtgaaggtgatgcaacatacggaaaacttacccttaaatttatttgcactactggaaaac
tacctgttccgtggccaacacttgtcactactttctcttatggtgttcaatgcttttcccgttatccggatcacatgaaacg
gcatgactttttcaagagtgccatgcccgaaggttatgtacaggaacgcactatatctttcaaagatgacgggaacta
caagacgcgtgctgaagtcaagtttgaaggtgatacccttgttaatcgtatcgagttaaaaggtattgattttaaagaa
gatggaaacattctcggacacaaactggagtacaactataactcacacaatgtatacatcacggcagacaaacaaa
gaatggaatcaaagctaacttcaaaattcgccacaacattgaagatggctccgttcaactagcagaccattatcaaca
aaatactccaattggcgatggccctgtccttttaccagacaaccattacctgtccacacaatctgccctttcgaaagatcc

FIG. 11C caacgaaaagcgtgaccacatggtccttcttgagtttgtaactgctgctgggattacacatggcatggatgagctcta
caaataaggatccaaactcgagtaaggatctccaggcatcaaataaaacgaaaggctcagtcgaaagactgggcctttcg
ttttatctgttgtttgtcggtgaacgctctctactagagtcacactggctcaccttcgggtgggcctttctgcgtttatacctagg
gcgttcggctgcggcgagcggtatcagctcactcaaaggcggtaatacgTCCCTGCTCGTCACGCTTTCAGGC
ACCGTGCCAGATATCGACGTGGAGTCGATCACTGTGATTGGCGAAGGGGAAGGCAGCGCTA
CCCAAATCGCTAGCTTGCTGGAGAAGCTGAAACAAACCACGGGCATTGATCTGGCGAAATC
CCTACCGGGTCAATCCGACTCGCCCGCTGCGAAGTCCTAAGAGATAGCGATGTGACCGCGAT
CGCTTGTCAAGAATCCCAGTGATCCCGAACCATAGGAAGGCAAGCTCAATGCTTGCCTCGTC
TTGAGGACTATCTAGATGTCTGTGGAACGCACATTTATTGCCATCAAGCCCGATGGCGTTCA
GCGGGGTTTGGTCGGTACGATCATCGGCCGCTTTGAGCAAAAAGGCTTCAAACTGGTGGGC
CTAAAGCAGCTGAAGCCCAGTCGCGAGCTGGCCGAACAGCACTATGCTGTCCACCGCGAGC
GCCCCTTCTTCAATGGCCTCGTCGAGTTCATCACCTCTGGGCCGATCGTGGCGATCGTCTTGG
AAGGCGAAGGCGTTGTGGCGGCTGCTCGCAAGTTGATCGGCGCTACCAATCCGCTGACGGC
AGAACCGGGCACCATCCGTGGTGATTTTGGTGTCAATATTGGCCGCAACATCATCCATGGCT
CGGATGCAATCGAAACAGCACAACAGGAAATTGCTCTCTGGTTTAGCCCAGCAGAGCTAAG
TGATTGGACCCCCACGATTCAACCCTGGCTGTACGAATAAGGTCTGCATTCCTTCAGAGAGA
CATTGCCATGCCC

FIG. 12A 5. pSe1Bb2°s-GFP (S195bp)

GATAATCTCATGACCAAAATCCCTTAACGTGAGTTTTCGTTCCACTGAGCGTCAGAC<u>CCCGTAGA</u>
<u>AAAGATCAAAGGATCTTCTTGAGATCCTTTTTTTCTGCGCGTAATCTGCTGCTTGCAAACAA</u>
<u>AAAAACCACCGCTACCAGCGGTGGTTTGTTTGCCGGATCAAGAGCTACCAACTCTTTTTCCG</u>
<u>AAGGTAACTGGCTTCAGCAGAGCGCAGATACCAAATACTGTTCTTCTAGTGTAGCCGTAGTT</u>
<u>AGGCCACCACTTCAAGAACTCTGTAGCACCGCCTACATACCTCGCTCTGCTAATCCTGTTACC</u>
<u>AGTGGCTGCTGCCAGTGGCGATAAGTCGTGTCTTACCGGGTTGGACTCAAGACGATAGTTAC</u>
<u>CGGATAAGGCGCAGCGGTCGGGCTGAACGGGGGGTTCGTGCACACAGCCCAGCTTGGAGC</u>
<u>GAACGACCTACACCGAACTGAGATACCTACAGCGTGAGCTATGAGAAAGCGCCACGCTTCC</u>
<u>CGAAGGGAGAAAGGCGGACAGGTATCCGGTAAGCGGCAGGGTCGGAACAGGAGAGCGCA</u>
<u>CGAGGGAGCTTCCAGGGGGAAACGCCTGGTATCTTTATAGTCCTGTCGGGTTTCGCCACCTC</u>
<u>TGACTTGAGCGTCGATTTTTGTGATGCTCGTCAGGGGGGCGGAGCCTATGGAAAA</u>ACGCCA
GCAACGCGGCCTTTTACGGTTCCTGGCCTTTTGCTGGCCTTTTGCTCACATGTGTGCTGGGCCC
<u>CAATGCCTTCTCCAAGGGCGGCATTCCCCTGACTGTTGAAGGCGTTGCCAATATCAAGATTG</u>
<u>CTGGGGAAGAACCGACCATCCACAACGCGATCGAGCGGCTGCTTGGCAAAAACCGTAAGG</u>
<u>AAATCGAGCAAATTGCCAAGGAGACCCTCGAAGGCAACTTGCGTGGTGTTTTAGCCAGCCT</u>
<u>CACGCCGGAGCAGATCAACGAGGACAAAATTGCCTTTGCCAAAAGTCTGCTGGAAGAGGC</u>
<u>GGAGGATGACCTTGAGCAGCTGGGTCAAGTCCTCGATACGCTGCAAGTCCAGAACATTTCC</u>
<u>GATGAGGTCGGTTATCTCTCGGCTAGTGGACGCAAGCAGCGGGCTGATCTGCAGCGAGATG</u>
<u>CCCGAATTGCTGAAGCCGATGCCCAGGCTGCCTCTGCGATCCAAACGGCCGAAAATGACAA</u>
<u>GATCACGGCCCTGCGTCGGATCGATCGCGATGTAGCGATCGCCCAAGCCGAGGCCGAGCGC</u>
<u>CGGATTCAGGATGCGTTGACGCGGCGCGAAGCGGTGGTGGCCGAAGCTGAAGCGGACATT</u>
<u>GCTACCGAAGTCGCTCGTAGCCAAGCAGAACTCCCTGTGCAGCAGGAGCGGATCAAACAG</u>
<u>GTGCAGCAGCAACTTCAAGCCGATGTGATCGCCCCAGCTGAGGCAGCTTGTAAACGGGCGA</u>
<u>TCGCGGAAGCGCGGGGGGCCGCCGCCCGTATCGTCGAAGATGGAAAAGCTCAAGCGGAAG</u>
<u>GGACCCAACGGCTGGCGGAGGCTTGGCAGACCGCTGGTGCTAATGCCCGCGACATCTTCCT</u>
<u>GCTCCAGAAG</u>TCTAGACCAGCCAGGACAGAAATGCCTCGACTTCGCTGCTACCCAAGGTTGCC
GGGTGACGCACACCGTGGAAACGGATGAAGGCACGAACCCAGTGGACATAAGCCTGTTCGGTT

FIG. 12B

CGTAAGCTGTAATGCAAGTAGCGTATGCGCTCACGCAACTGGTCCAGAACCTTGACCGAACGC
AGCGGTGGTAACGGCGCAGTGGCGGTTTTCATGGCTTGTTATGACTGTTTTTTTGGGGTACA
GTCTATGCCTCGGGCATCCAAGCAGCAAGCGCGTTACGCCGTGGGTCGATGTTTGATGTTAT
GGAGCAGCAACGATGTTACGCAGCAGGGCAGTCGCCCTAAAACAAAGTTAAACATTATGA
GGGAAGCGGTGATCGCCGAAGTATCGACTCAACTATCAGAGGTAGTTGGCGTCATCGAGCG
CCATCTCGAACCGACGTTGCTGGCCGTACATTTGTACGGCTCCGCAGTGGATGGCGGCCTGA
AGCCACACAGTGATATTGATTTGCTGGTTACGGTGACCGTAAGGCTTGATGAAACAACGCG
GCGAGCTTTGATCAACGACCTTTTGGAAACTTCGGCTTCCCCTGGAGAGAGCGAGATTCTC
CGCGCTGTAGAAGTCACCATTGTTGTGCACGACGACATCATTCCGTGGCGTTATCCAGCTAA
GCGCGAACTGCAATTTGGAGAATGGCAGCGCAATGACATTCTTGCTGGTATCTTCGAGCCA
GCCACGATCGACATTGATCTGGCTATCTTGCTGACAAAAGCAAGAGAACATAGCGTTGCCTT
GGTAGGTCCAGCGGCGGAGGAACTCTTTGATCCGGTTCCTGAACAGGATCTATTTGAGGCG
CTAAATGAAACCTTAACGCTATGGAACTCGCCGCCCGACTGGGCTGGCGATGAGCGAAATG
TAGTGCTTACGTTGTCCCGCATTTGGTACAGCGCAGTAACCGGCAAAATCGCGCCGAAGGAT
GTCGCTGCCGACTGGGCAATGGAGCGCCTGCCGGCCCAGTATCAGCCCGTCATACTTGAAG
CTAGACAGGCTTATCTTGGACAAGAAGAAGATCGCTTGGCCTCGCGCGCAGATCAGTTGGA
AGAATTTGTCCACTACGTGAAAGGCGAGATCACCAAGGTAGTCGGCAAATAACCtcattttcgcc
agatatcgacgtcttaagacccactttcacatttaagttgtttttctaatccgcatatgatcaattcaaggccgaataagaa
ggctggctctgcaccttggtgatcaaataattcgatagcttgtcgtaataatggcggcatactatcagtagtaggtgtt
tccctttcttctttagcgacttgatgctcttgatcttccaatacgcaacctaaagtaaaatgccccacagcgctgagtgca
tataatgcattctctagtgaaaaaccttgttggcataaaaaggctaattgattttcgagagtttcatactgttttctgtag
gccgtgtacctaaatgtacttttgctccatcgcgatgacttagtaaagcacatctaaaacttttagcgttattacgtaaaa
aatcttgccagctttcccccttctaaagggcaaaagtgagtatggtgcctatctaacatctcaatggctaaggcgtcgag
caaagcccgcttatttttacatgccaatacaatgtaggctgctctacacctagcttctgggcgagtttacgggttgtta
aaccttcgattccgacctcattaagcagctctaatgcgctgttaatcactttacttttatctaatctagacatcattaattcc
taattttgttgacactctatcgttgatagagttattttaccactccctatcagtgatagagattgacatccctatcagtga
tagagaTATAATGGCCACTAaaagaattcaaaagatctttaagaaggagatatacatatgagtaaaggagaag
aacttttcactggagttgtcccaattcttgttgaattagatggtgatgttaatgggcacaaattttctgtcagtggagag
ggtgaaggtgatgcaacatacggaaaacttacccttaaatttatttgcactactggaaaactacctgttccgtggccaa

FIG. 12C cacttgtcactactttctcttatggtgttcaatgcttttcccgttatccggatcacatgaaacggcatgacttttcaagag
tgccatgcccgaaggttatgtacaggaacgcactatatctttcaaagatgacgggaactacaagacgcgtgctgaag
tcaagtttgaaggtgataccccttgttaatcgtatcgagttaaaaggtattgatttttaaagaagatggaaacattctcgg
acacaaactggagtacaactataactcacacaatgtatacatcacggcagacaaacaaaagaatggaatcaaagcta
acttcaaaattcgccacaacattgaagatggctccgttcaactagcagaccattatcaacaaaatactccaattggcga
tggccctgtccttttaccagacaaccattacctgtccacacaatctgcccttttcgaaagatcccaacgaaaagcgtgacc
acatggtccttcttgagtttgtaactgctgctgggattacacatggcatggatgagctctacaaataaggatccaaactc
gagtaaggatctccaggcatcaaataaaacgaaaggctcagtcgaaagactgggcctttcgttttatctgttgtttgtcggtg
aacgctctctactagagtcacactggctcaccttcgggtgggcctttctgcgtttatacctagggcgttcggctgcggcgagc
ggtatcagctcactcaaaggcggtaatacgTCCCTGCTCGTCACGCTTTCAGGCACCGTGCCAGATATC
GACGTGGAGTCGATCACTGTGATTGGCGAAGGGGAAGGCAGCGCTACCCAAATCGCTAGCT
TGCTGGAGAAGCTGAAACAAACCACGGGCATTGATCTGGCGAAATCCCTACCGGGTCAATC
CGACTCGCCCGCTGCGAAGTCCTAAGAGATAGCGATGTGACCGCGATCGCTTGTCAAGAATC
CCAGTGATCCCGAACCATAGGAAGGCAAGCTCAATGCTTGCCTCGTCTTGAGGACTATCTAG
ATGTCTGTGGAACGCACATTTATTGCCATCAAGCCCGATGGCGTTCAGCGGGGTTTGGTCGG
TACGATCATCGGCCGCTTTGAGCAAAAAGGCTTCAAACTGGTGGGCCTAAAGCAGCTGAA
GCCCAGTCGCGAGCTGGCCGAACAGCACTATGCTGTCCACCGCGAGCGCCCCTTCTTCAATG
GCCTCGTCGAGTTCATCACCTCTGGGCCGATCGTGGCGATCGTCTTGGAAGGCGAAGGCGTT
GTGGCGGCTGCTCGCAAGTTGATCGGCGCTACCAATCCGCTGACGGCAGAACCGGGCACCA
TCCGTGGTGATTTTGGTGTCAATATTGGCCGCAACATCATCCATGGCTCGGATGCAATCGAA
ACAGCACAACAGGAAATTGCTCTCTGGTTTAGCCCAGCAGAGCTAAGTGATTGGACCCCCA
CGATTCAACCCTGGCTGTACGAATAAGGTCTGCATTCCTTCAGAGAGACATTGCCATGCCC

EXPRESSION VECTOR FOR CYANOBACTERIA

CROSS-REFERENCE TO RELATED APPLICATION

This application claims priority to Korean Patent Application No. 10-2014-0177540, filed on Dec. 10, 2014, and all the benefits accruing therefrom under 35 U.S.C. §119, the contents of which in its entirety are herein incorporated by reference.

BACKGROUND

1. Field

The present disclosure relates to an expression vector which is capable of producing desired substances by transforming cyanobacteria. The present disclosure also relates to a vector that can be used for both cyanobacteria and *E. coli*, a host cell transformed with the vector, a method for producing a substance using the transformed host cell, and a method for preparing a multivector using the vector.

[Description about National Research and Development Support]

This study was supported by Ministry of Science, ICT and Future Planning, Republic of Korea (Cooperation research project: KCRC CCS2020 Business, Project No. 2014M1A8A1049277) under the superintendence of the Korea Carbon Capture & Sequestration R&D Center.

2. Description of the Related Art

At present, cutting-edge metabolic engineering techniques such as next-generation genome sequencing and fast DNA synthesis are employed to produce useful bioproducts. The production of bioproducts using *E. coli*, yeast or *Corynebacterium*, which are the most widely used industrially at present, is being continuously developed. For the production of foreign metabolites, it is essential to reconstitute required heterologous genes in cells. Also, an optimization process for maximizing the production of the target substance is necessary. A generally adopted method for constructing a heterologous metabolic pathway for producing the target substance is to insert a specific gene into a plasmid or genome. More recently, advanced cloning techniques such as sequence and ligase-independent cloning (SLIC), Gibson DNA assembly, circular polymerase extension cloning (OPEC), etc. are being used.

SUMMARY

In an aspect, the present disclosure is directed to providing an expression vector which is operable in cyanobacteria.

In another aspect, the present disclosure is directed to providing a vector which can transform cyanobacteria after being inserted into the cyanobacterial genome.

In another aspect, the present disclosure is directed to providing a vector which is operable in both cyanobacteria and *E. coli*.

In another aspect, the present disclosure is directed to providing a vector having two or more target genes being inserted and capable of expressing two or more kinds of proteins simultaneously.

In another aspect, the present disclosure is directed to providing a vector which operates effectively in the industrially useful *Synechococcus elongatus* PCC 7942.

In another aspect, the present disclosure is directed to providing an expression vector capable of effectively producing industrially useful substances and a host cell transformed with the vector.

In another aspect, the present disclosure is directed to providing a method for effectively producing industrially useful substances.

In another aspect, the present disclosure is directed to providing a method for preparing a multivector which expresses two or more target proteins that can invoke a mechanism for producing a useful substance or themselves can be industrially useful.

In another aspect, the present disclosure is directed to providing a vector which can maintain strong expression even when a host cell to which the vector is introduced is in a stationary phase.

In an aspect, the present disclosure provides an expression vector for cyanobacteria, the expression vector containing, sequentially, a pUC replication origin as a replication origin; a spectinomycin-resistant gene as a selection marker; and a promoter selected from a group consisting of a trc promoter, a tetA promoter or a modified tetA promoter, a BAD promoter and a cbbL promoter.

In another aspect, the present disclosure provides a host cell transformed with the vector.

In another aspect, the present disclosure provides a method for producing a substance, which includes culturing the transformed host cell.

In another aspect, the present disclosure provides a method for preparing a multivector containing two or more target genes, the method including inserting the target genes into the vector according to an exemplary embodiment of the present disclosure, wherein the vector already contains one or more preexisting target gene before the insertion of another target genes, and the insertion includes forming complementary binding between the BglII site located upstream of the preexisting target gene of the vector or the another target gene to be inserted into the vector and the BamHI site located downstream of the preexisting target gene of the vector or the another target gene to be inserted into the vector.

Cyanobacteria such as *Synechococcus elongatus* are photosynthetic microorganisms that can grow using light and carbon dioxide only like higher plants. Since the vector disclosed in the present disclosure is operable in cyanobacteria such as *Synechococcus elongatus*, it can produce a variety of biofuel substitutes or chemical products. Also, the vector may simultaneously express two or more target proteins that can invoke a mechanism for producing a useful substance or the target proteins themselves may be industrially useful. In another aspect, the present disclosure may provide a vector which can maintain strong expression even when its host cell is in stationary phase. Furthermore, time and cost can be saved remarkably and gene expression level can be controlled effectively because of simple gene assembly. In addition, mutation rate can be significantly reduced because transformation is conducted following restriction enzyme treatment and ligation without having to perform PCR. Furthermore, the vector can be usefully used as a gene expression tool since *Synechococcus elongatus* mainly transforms the target gene on its genome.

BRIEF DESCRIPTION OF THE DRAWINGS

FIG. 8A~FIG. 8C show the full sequence (SEQ ID NO: 1) of a pSe1Bb1s-GFP vector.

FIG. 9A~FIG. 9C show the full sequence (SEQ ID NO: 2) of a pSe1Bb2s-GFP vector.

FIG. 10A~FIG. 10C show the full sequence (SEQ ID NO: 3) of a pSe1Bb8s-GFP vector.

FIG. 11A~FIG. 11C show the full sequence (SEQ ID NO: 4) of a pSe1Bb$_{cbbL}$s-GFP vector.

FIG. 12A~FIG. 12C show the full sequence (SEQ ID NO: 5) of a pSe1Bb2$^O$s-GFP vector.

DETAILED DESCRIPTION

Figure 1:
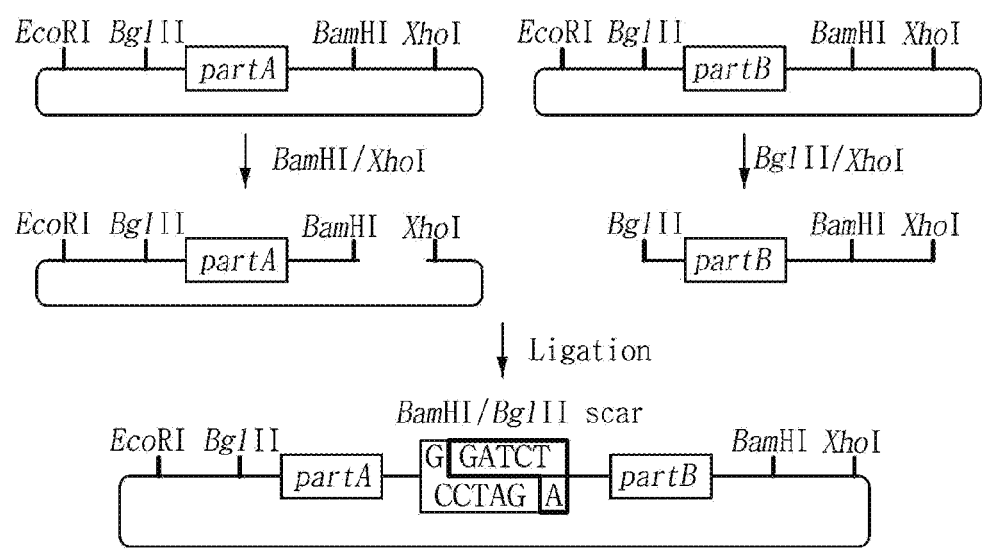
FIG. 1 schematically describes BglBrick cloning.

The vector disclosed in the present disclosure is also called a SyneBrick vector.

*Synechococcus elongatus*, one of cyanobacteria, is a photosynthetic microorganism that can grow using light and carbon dioxide only like higher plants. Due to this characteristic, the strain is gaining attentions worldwide as an environment-friendly microorganism. Unlike eukaryotic microalgae, the prokaryotic cyanobacteria are easy to be genetically modified to alter metabolic pathways or artificially regulate metabolites. A synthetic biological/metabolic engineering technique based on the genetic modification technology may be introduced to *Synechococcus elongatus* in order to produce a variety of biofuel substitutes or chemical products using metabolic pathways that have not existed.

In the present disclosure, a "multivector" refers to a vector which contains two or more target genes or two or more kinds of target genes desired to be overexpressed and is able to express two or more, or two or more kinds of target proteins simultaneously. The expressed two or more proteins may be industrially useful themselves, or the two or more proteins may invoke a mechanism for producing desired useful substances.

In the vector disclosed in the present disclosure, the genes are linked operably to each other. The term "operably" means that the target genes can be expressed normally.

In an aspect, the present disclosure provides an expression vector for cyanobacteria, which contains, sequentially: a pUC replication origin as a replication origin; a spectinomycin-resistant gene as a selection marker; and a promoter selected from a group consisting of a trc promoter, a tetA promoter or a modified tetA promoter, a BAD promoter and a cbbL promoter.

In an exemplary embodiment, the modified tetA promoter may include a sequence of SEQ ID NO 6.

Since the vector can be used for both cyanobacteria and *E. coli*, gene recombination can be easily achieved in *E. coli* and a desired protein may be obtained by transforming into cyanobacteria.

In an exemplary embodiment, the vector may further contain a repressor selected from a group consisting of a lacI repressor, a tetR repressor and an AraC repressor upstream of the promoter.

In an exemplary embodiment, the vector may further contain a neutral site (NSI) derived from *Synechococcus elongatus* PCC 7942 upstream or downstream of the replication origin. For example, the neutral site may include: NSIa including a sequence of SEQ ID NO 7; and NSIb including a sequence of SEQ ID NO 8. In an exemplary embodiment, the vector may be inserted onto the genome of *Synechococcus elongatus* PCC 7942 via the neutral site.

For example, a template vector of the expression vector for cyanobacteria may be a pBbE1c-RFP vector (Lee T S, Krupa R A, Zhang F, Hajimorad M, Holtz W J, Prasad N, Lee S K, Keasling J D (2011b) BglBrick vectors and datasheets: a synthetic biology platform for gene expression. *J Biol Eng* 5:12). In addition, for example, the spectinomycin-resistant gene, the NSIa, the NSIb and the pUC may be derived from pSyn_1 (Invitrogen).

The vector may further contain a green fluorescent protein (GFP) gene downstream of the promoter. Since the green fluorescent protein (GFP) gene emits fluorescence when expressed in a host cell, it can tell whether the vector operates appropriately and the target gene is expressed normally. Another target gene may be inserted at the green fluorescent protein (GFP) gene site. A BglII site and a BamHI site, which are restriction enzyme sites, may be located on both sides of the green fluorescent protein (GFP) gene.

For example, the green fluorescent protein (GFP) gene may be derived from pBbB5k-GFP (Lee T S, Krupa R A, Zhang F, Hajimorad M, Holtz W J, Prasad N, Lee S K, Keasling J D (2011b) BglBrick vectors and datasheets: a synthetic biology platform for gene expression. *J Biol Eng* 5:12).

In another exemplary embodiment, the vector may further contain a BglII site and a BamHI site as restriction enzyme sites. In another exemplary embodiment, the vector may further contain an EcoRI site, a BglII site, a BamHI and an XhoII site as restriction enzyme sites.

In another exemplary embodiment, the vector may further contain a target gene which encodes a target protein desired to be overexpressed.

In another exemplary embodiment, the vector may contain two or more target genes.

In an exemplary embodiment, the two or more target genes may be derived from different vectors. Each of the different vectors may have a BglII site and a BamHI site on both sides of the target gene, and the two target genes may be included in one vector by complementary binding between the BglII site of one vector and the BamHI site of the other vector through restriction enzyme treatment.

BglBrick cloning is a cloning method not requiring a PCR amplification step. According to the method, target genes A and B included in different vectors may be easily cloned into one vector. For example, referring to FIG. 1, each vector has EcoRI, BglII, BamHI and XhoI sites as restriction enzymes such that a target gene partB can be bound immediately downstream of a target gene partA. It is possible because, upon enzymatic treatment by BamHI and BglII, the complementary DNA strands can bind again to each other. In this way, various genes can be easily cloned into one vector.

Figure 2:
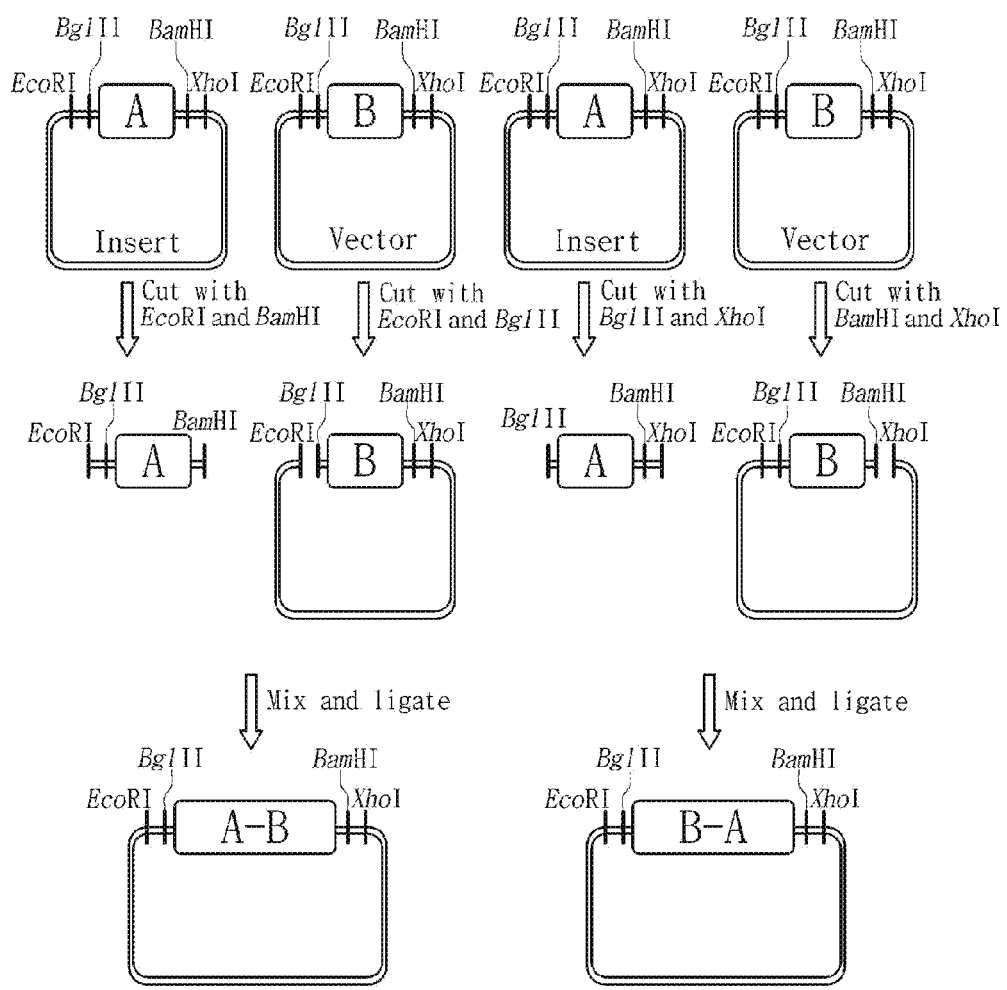
FIG. 2 schematically describes a procedure of obtaining a vector in which target genes A-B and target genes B-A are inserted using BglBrick cloning.

In an exemplary embodiment, the BglII site and the BamHI site may be located on both sides of the target gene. In another exemplary embodiment, the order of the target gene and the restriction enzyme sites may be EcoRI→BglII site→target gene→BamHI site→XhoII site. For example, let's suppose a vector A and a vector B as two vectors having such an order and having a target gene A and a target gene B, respectively. By treating the vector A with the restriction enzymes EcoRI and BamHI and treating the vector B with the restriction enzymes EcoRI and BglII, and then ligating them by complementarily binding the sites cleaved by BalII and BamHI, a vector in which the target genes A-B are inserted can be obtained (FIG. 2). Conversely, by treating the vector A with BglII and XhoI and treating the vector B with BamHI and XhoI, and then performing ligation, the target genes may be inserted in the order of B-A (FIG. 2).

In an exemplary embodiment, the vector may be a pSe1Bb1s-GFP vector containing a lacI repressor and a trc promoter. In an exemplary embodiment, the vector may have a sequence of SEQ ID NO 1.

The locations of major parts of the pSe1Bb1s-GFP vector (SEQ ID NO 1) are as follows:
pUC origin: 58-673
NSIa: 745-1543
spectinomycin-resistant gene: 1684-2694
lacI repressor: 2790-3881
trc promoter: 3938-4172
green fluorescent protein: 4187-4923
NSIb: 5132-5907.

In an exemplary embodiment, the vector may be a pSe1Bb2s-GFP vector containing a tetR repressor and a tetA promoter. In an exemplary embodiment, the vector may have a sequence of SEQ ID NO 2.

The locations of major parts of the pSe1Bb2s-GFP vector (SEQ ID NO 2) are as follows:
pUC origin: 58-673
NSIa: 745-1543
spectinomycin-resistant gene: 1684-2694
tetR repressor: 2721-3347
tetA promoter: 3348-3420
green fluorescent protein: 3436-4172
NSIb: 4381-5156.

In an exemplary embodiment, the vector may be a pSe1Bb8s-GFP vector containing an AraC repressor and a BAD promoter. In another exemplary embodiment, the vector may have a sequence of SEQ ID NO 3.

The locations of major parts of the pSe1Bb8s-GFP vector (SEQ ID NO 3) are as follows:
pUC origin: 58-673
NSIa: 745-1543
spectinomycin-resistant gene: 1684-2694
AraC repressor: 2721-3599
BAD promoter: 3875-3902
green fluorescent protein: 3940-4676
NSIb: 4885-5660.

In an exemplary embodiment, the vector may be a pSe1Bb$_{cbbL}$s-GFP vector containing a cbbL promoter. In another exemplary embodiment, the vector may have a sequence of SEQ ID NO 4.

The locations of major parts of the pSe1Bb$_{cbbL}$s-GFP vector (SEQ ID NO 4) are as follows:
pUC origin: 58-673
NSIa: 745-1543
spectinomycin-resistant gene: 1684-2694
cbbL promoter: 2724-2934
green fluorescent protein: 2950-3686
NSIb: 3895-4670.

In an exemplary embodiment, the vector may be a pSe1Bb2$^O$s-GFP vector containing a TetR repressor and a modified tetA promoter including a sequence of SEQ ID NO 6. In another exemplary embodiment, the vector may have a sequence of SEQ ID NO 5.

The locations of major parts of the pSe1Bb2$^O$s-GFP vector (SEQ ID NO 5) are as follows:
pUC origin: 58-673
NSIa: 745-1543
spectinomycin-resistant gene: 1684-2694
tetR repressor: 2721-3347
modified tet A promoter: 3348-3459
green fluorescent protein: 3475-4211
NSIb: 4420-5195.

For example, the pSe1Bb1s-GFP SyneBrick vector may be constructed by constructing a pSe1Bb1s-RFP vector using the BglBrick vector pBbE1c-RFP published in the literature and pSyn_1 purchased from Invitrogen through OPEC cloning and then ligating pBbB5k-GFP whose GFP gene has been cleaved using a specific restriction enzyme to the pSe1Bb1s-RFP except for the RFP part. Subsequently, in order to construct various SyneBrick vectors by changing the gene expression regulating part, pSe1Bb2s-GFP and pSe1Bb8s-GFP may be obtained by cleaving the promoter and repressor parts of pBbE2c-RFP and pBbE8c-RFP respectively using specific restriction enzymes (AatII/EcoRI) and then inserting them after removing the promoter and repressor parts of pSe1Bb1s-GFP.

In addition, for example, after amplifying the promoter part possessed by a *Synechococcus* strain using a primer [5'-AAA GAC GTC ATC TCG CTT CTG G-3' (SEQ ID NO 9)/5'-TTT GAA TTC GTC GTC TCT CCC T-3' (SEQ ID NO 10)] and then treating with the restriction enzymes AatII and EcoRI, it may be inserted into the pSe1Bb1s-GFP vector having the promoter and repressor parts removed.

In order to improve the induction rate of the SyneBrick vector pSe1Bb2s-GFP containing the tetA promoter, an operator sequence may be further added so as to enhance the function of the repressor. The tetR part and the promoter part including the modified operator sequence may be prepared through DNA synthesis and then inserted into a pSe1Bb1s-GFP vector having the promoter and repressor parts removed using the AatII/EcoRI restriction enzyme to construct pSe1Bb2$^O$s-GFP.

In another aspect, the present disclosure provides a transformed host cell transformed with one of the above-described vectors. The host cell may be cyanobacterium. Cyanobacteria such as *Synechococcus elongatus* are photosynthetic microorganisms that can grow using light and carbon dioxide only like higher plants. Since the vector disclosed in the present disclosure is operable in cyanobacteria such as *Synechococcus elongatus*, it can produce a variety of biofuel substitutes or chemical products. In an exemplary embodiment, the cyanobacterium may be *Synechococcus elongatus* PCC 7942.

In another aspect, the present disclosure provides a method for producing a substance, which includes culturing the transformed host cell. Two or more kinds of proteins may be produced simultaneously by the method. The produced two or more proteins may invoke a mechanism for producing industrially useful substances. In addition, the proteins themselves may be industrially useful.

In another aspect, the present disclosure provides a method for preparing a multivector containing two or more target genes. For example, the method may include inserting the target genes into the vector according to an exemplary embodiment of the present disclosure. The vector may already contain one or more preexisting target gene before the insertion of the new target genes. And, the insertion may include forming complementary binding between the BglII site located upstream of the preexisting target gene of the vector or another target gene to be inserted into the vector and the BamHI site located downstream of the preexisting target gene of the vector or another target gene to be inserted into the vector.

In an exemplary embodiment, the complementary binding may be formed between the BglII site located upstream of the preexisting target gene of the vector and the BamHI site located downstream of another target gene to be inserted into the vector, and, as a result of the complementary binding, the inserted target gene may be inserted upstream of the preexisting target gene in the vector. For example, referring to the left side of FIG. 2, a procedure whereby a target gene A is inserted into a vector already having a target gene B in the order of A-B is described. The target gene A to be inserted is designed to have EcoRI and BglII restriction enzyme sites upstream thereof and a BamHI restriction enzyme site downstream thereof. For this purpose, a vector having the target gene A and having EcoRI and BglII restriction enzyme sites upstream of A, and BamHI and XhoI restriction enzyme sites downstream thereof may be used. By treating the vector with restriction enzymes EcoRI and BamHI, the target gene A having EcoRI and BglII restriction enzyme sites upstream thereof and a BamHI restriction enzyme site downstream thereof may be obtained. Meanwhile, a vector having the target gene B and having EcoRI and BglII restriction enzyme sites upstream of B, and BamHI and XhoI restriction enzyme sites downstream thereof may be treated with restriction enzymes EcoRI and BglII. When the vectors containing the target gene A and the target gene B are mixed, complementary binding may occur between the BglII site located upstream of the target gene B of the vector and the BamHI site located downstream of the target gene A to be inserted into the vector and, as a result, a vector wherein the target genes are inserted in the order of A-B may be obtained.

In another exemplary embodiment, the complementary binding may be formed between the BglII site located upstream of another target gene to be inserted into the vector and the BamHI site located downstream of the preexisting target gene of the vector, and, as a result of the complementary binding, the inserted target gene may be inserted downstream of the preexisting target gene in the vector. For example, referring to the right side of FIG. 2, a procedure whereby a target gene A is inserted into a vector already having a target gene B in the order of B-A is described. The target gene A to be inserted is designed to have a BamHI restriction enzyme site upstream thereof and BamHI and XhoI restriction enzyme sites downstream thereof. For this purpose, a vector having the target gene A and having EcoRI and BglII restriction enzyme sites upstream of A, and BamHI and XhoI restriction enzyme sites downstream thereof may be used. By treating the vector with restriction enzymes BglII and XhoI, the target gene A having a BglII restriction enzyme site upstream thereof and BamHI and XhoI restriction enzyme sites downstream thereof may be obtained. Meanwhile, a vector having the target gene B and having EcoRI and BglII restriction enzyme sites upstream of B and BamHI and XhoI restriction enzyme sites downstream thereof may be treated with restriction enzymes BamHI and XhoI. When the vectors containing the target gene A and the target gene B are mixed, complementary binding may occur between the BamHI site located downstream of the target gene B of the vector and the BglII site located upstream of the target gene A to be inserted into the vector and, as a result, a vector wherein the target genes are inserted in the order of B-A may be obtained.

In another exemplary embodiment, the method may further include, before the insertion, preparing a restriction enzyme site-containing target gene having a BglII site upstream of the target gene to be inserted and a BamHI site downstream of the target gene to be inserted. The restriction enzyme site-containing target gene may be prepared according to any method known in the art. For example, as described above, a vector having the target gene to be inserted and having EcoRI and BglII restriction enzyme sites upstream of the target gene and BamHI and XhoI restriction enzyme sites downstream of the target gene may be used.

Figure 3:
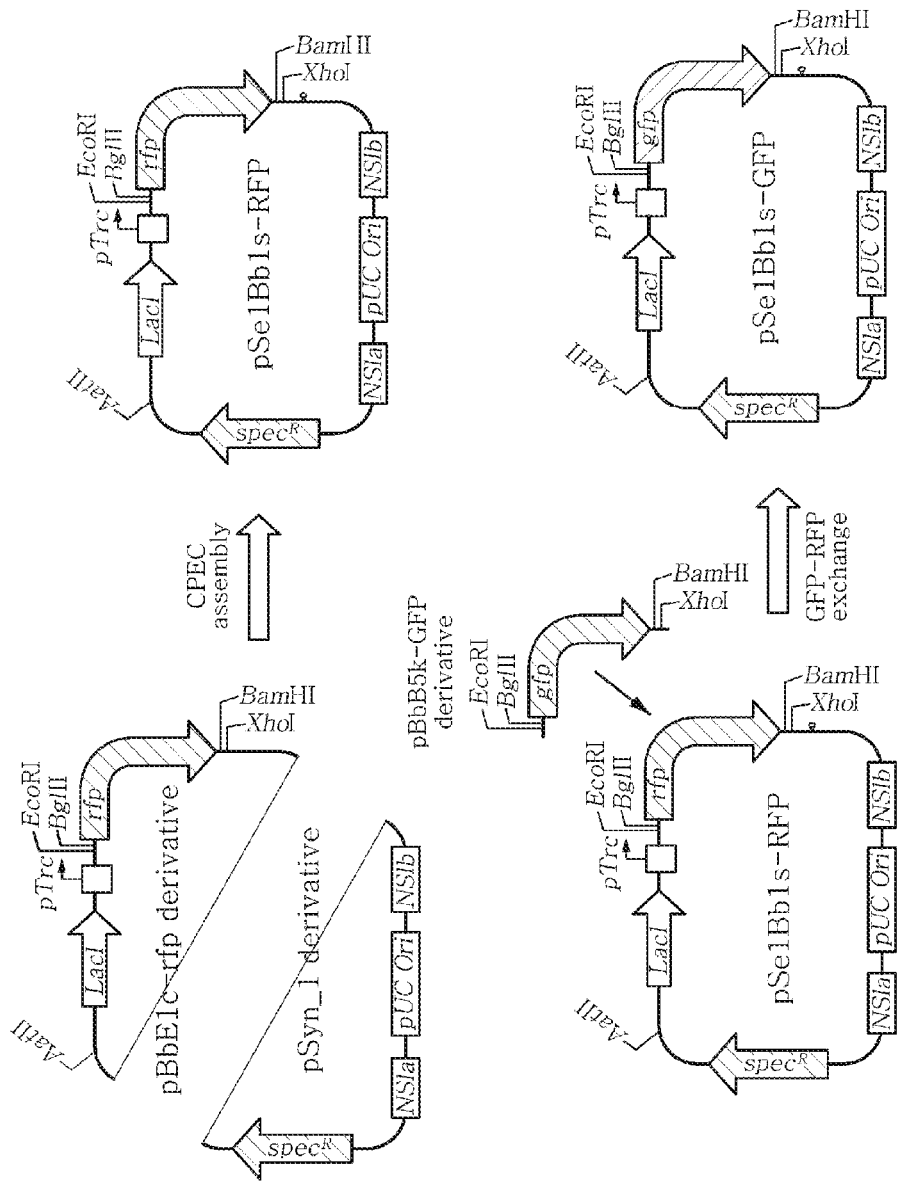
FIG. 3 schematically describes development of a pSe1Bb1s-GFP vector as one of SyneBrick vectors using the OPEC method.
Figure 4A:
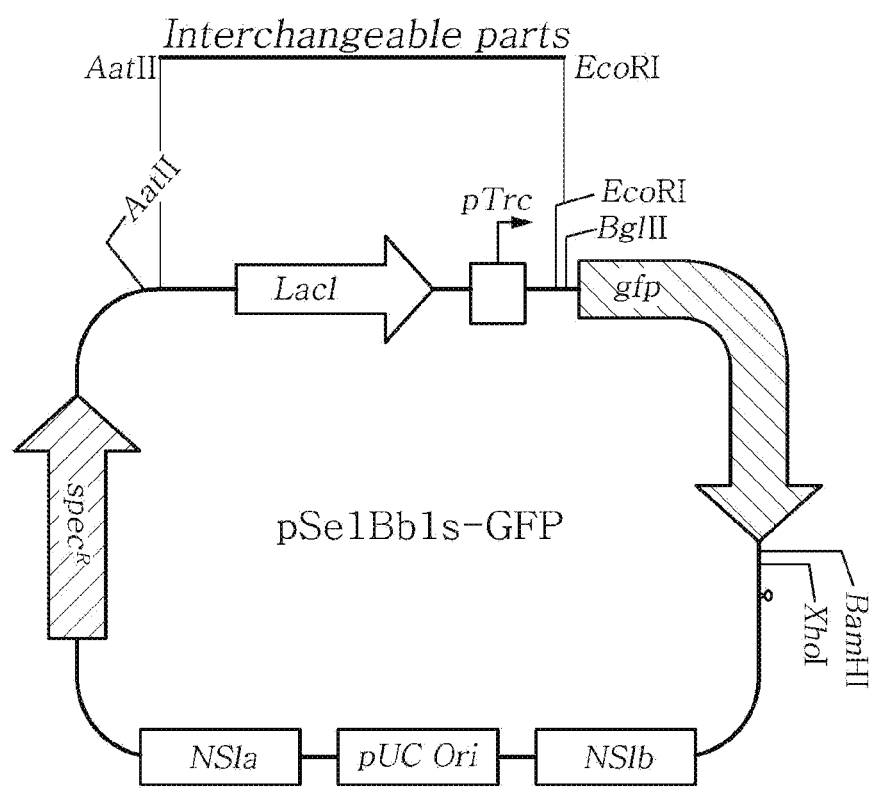
FIG. 4 schematically describes assembly of pSe1Bb2s-GFP, pSe1Bb8s-GFP, pSe1Bb2$^O$s-GFP and pSe1Bb$_{cbbL}$s-GFP vectors as SyneBrick vectors through PCR amplification, restriction enzyme treatment and ligation.
Figure 4B:
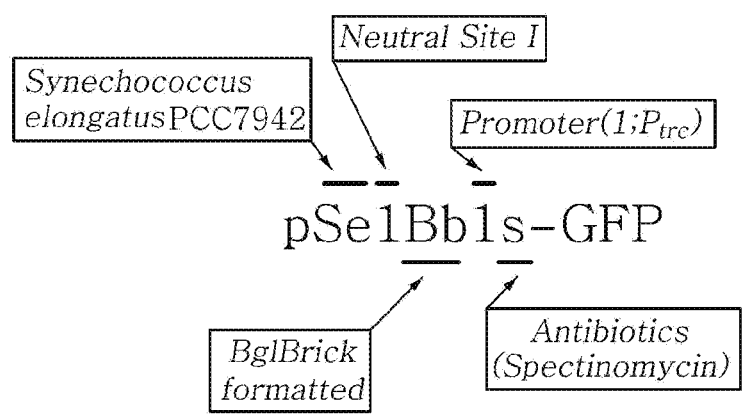
Figure 4C:
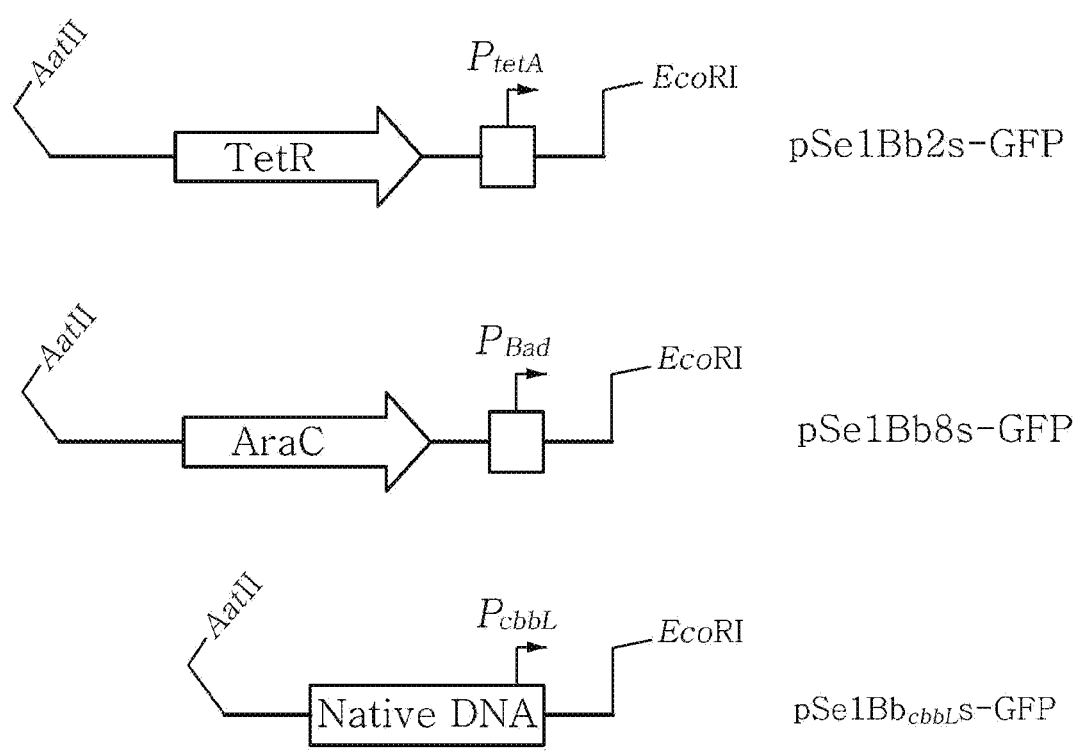
Figure 4D:
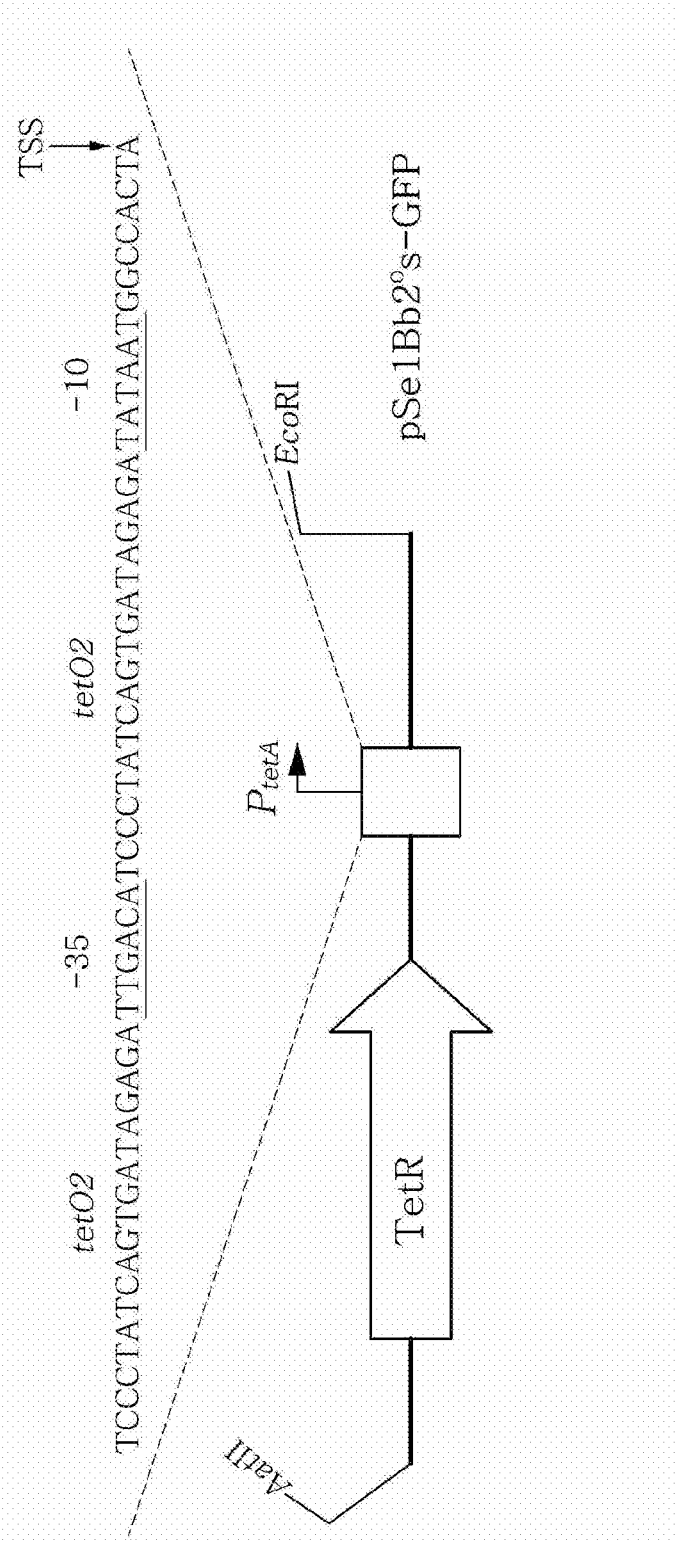

[Example 1] Construction of Novel SyneBrick Vector pSe1Bb1s-GFP pBbE1c-RFP (Lee T S, Krupa R A, Zhang F, Hajimorad M, Holtz W J, Prasad N, Lee S K, Keasling J D (2011b) BglBrick vectors and datasheets: a synthetic biology platform for gene expression. *J Biol Eng* 5:12) and pSyn_1 from Invitrogen were used to construct a SyneBrick vector pSe1Bb1s-GFP. Specifically, the lacI, ptrc and RFP parts of pBbE1c-RFP were amplified by PCR and the spectinomycin-resistant gene, NSIa, NS1b and pUC replication origin parts of pSyn_1 were amplified by PCR. Then, the novel SyneBrick vector was completed by combining the two PCR products through OPEC cloning (Quan J, Tian J (2009) Circular Polymerase Extension Cloning of Complex Gene Libraries and Pathways. *PLoS ONE* 4(7): e6441. doi:10.1371/journal.pone.0006441). In order to replace the RFP part of the vector with GFP, the RFP part was removed using EcoRI/XhoI restriction enzymes and the GFP part of another BglBrick vector pBbB5k-GFP (Lee T S, Krupa R A, Zhang F, Hajimorad M, Holtz W J, Prasad N, Lee S K, Keasling J D (2011b) BglBrick vectors and datasheets: a synthetic biology platform for gene expression. *J Biol Eng* 5:12) was inserted using EcoRI/XhoI restriction enzymes and a ligase. The vector was transformed into *E. coli* HIT-DH5α (Cat# RH617-J80, RBC Bioscience) and then extracted by miniprep. Since the assembled vector might have been mutated during the PCR procedure, its full sequence was identified through plasmid sequencing. The final SyneBrick vector with the DNA sequence confirmed was named as pSe1Bb1s-GFP (FIG. 3).

[Example 2] Construction of pSe1Bb2s-GFP, pSe1Bb8s-GFP, pSe1Bb$_{cbbL}$s-GFP and pSe1Bb2$^O$s-GFP Using SyneBrick Vector pSe1Bb1s-GFP The pSe1Bb1s-GFP prepared in Example 1 and previously known pBbE2c-RFP (Lee T S, Krupa R A, Zhang F, Hajimorad M, Holtz W J, Prasad N, Lee S K, Keasling J D (2011b) BglBrick vectors and datasheets: a synthetic biology platform for gene expression. *J Biol Eng* 5:12) and pBbE8c-RFP (Lee T S, Krupa R A, Zhang F, Hajimorad M, Holtz W J, Prasad N, Lee S K, Keasling J D (2011b) BglBrick vectors and datasheets: a synthetic biology platform for gene expression. *J Biol Eng* 5:12) were used to construct SyneBrick vectors pSe1Bb2s-GFP, pSe1Bb8s-GFP, pSe1Bb$_{cbbL}$s-GFP and pSe1Bb2$^O$s-GFP. The meaning of the alphabets and numbers in the plasmid name can be understood from FIG. 4, B.

Since the repressor and promoter parts of the BglBrick vectors pBbE2c-RFP and pBbE8c-RFP and the SyneBrick vector pSe1Bb1s-GFP share AatII/EcoRI restriction enzymes, the promoter and repressor parts of pSe1Bb1s-GFP were removed with AatII/EcoRI restriction enzymes and the promoter and repressor parts of pBbE2c-RFP and pBbE8c-RFP were inserted (FIG. 4, C).

In order to construct a SyneBrick vector using a promoter possessed by a *Synechococcus* strain, the part presumed to be the promoter of the cbbL gene was amplified using primers [5'-AAA GAC GTC ATC TCG CTT CTG G-3' (SEQ ID NO 9)/5'-TTT GAA TTC GTC GTC TCT CCC T-3' (SEQ ID NO 10)] and inserted into the pSe1Bb1s-GFP vector whose promoter and repressor parts had been removed by treating with AatII and EcoRI restriction enzymes. The resulting SyneBrick vector was named as pSe1Bb$_{cbbL}$s-GFP (FIG. 4, C).

When fluorescence emission was measured, pSe1Bb2s-GFP showed little difference in gene expression levels between in the presence and in the absence of an inducer. Therefore, in order to construct a modified model, a DNA was synthesized by attaching one more operator sequence of the promoter part (see FIG. 4, D showing a nucleotide of positions 52-109 of SEQ ID NO: 6) and then inserted using AatII/EcoRI restriction enzymes. The constructed SyneBrick vector was named as pSe1Bb2$^O$s-GFP.

Figure 5:
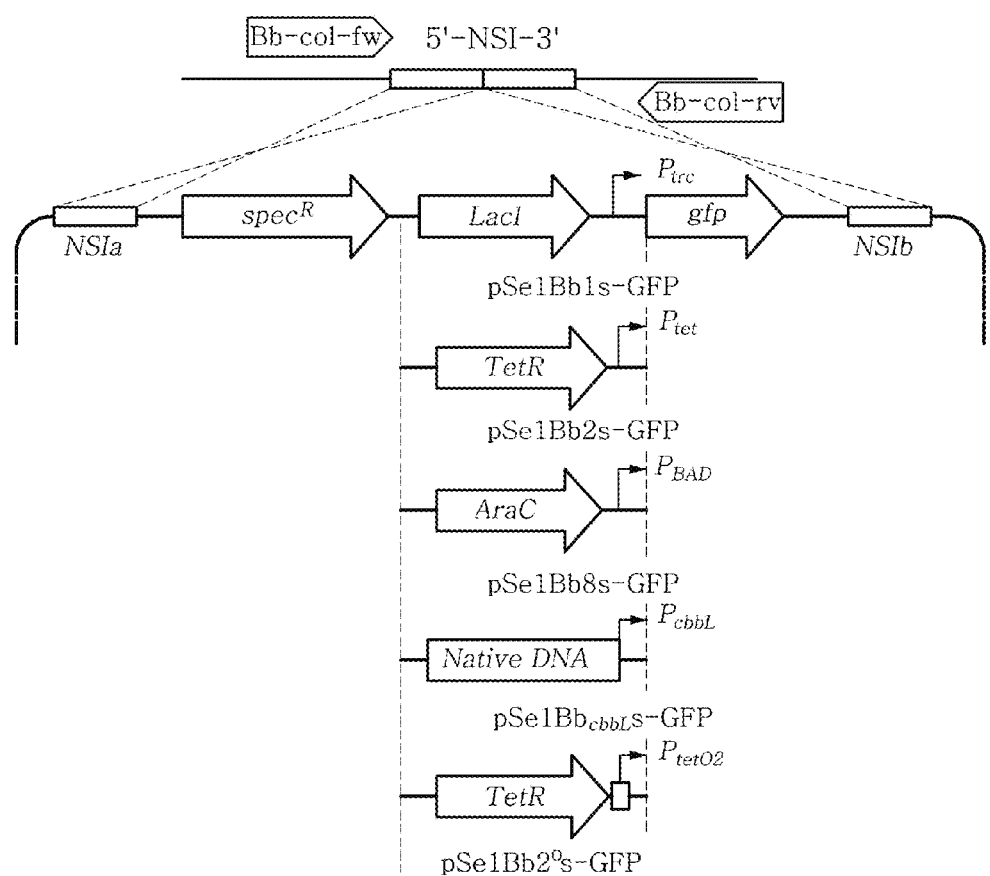
FIG. 5 schematically describes transformation of 5 SyneBrick vectors into *Synechococcus elongatus* strains.

Each of the prepared 5 SyneBrick vectors was transformed into a wild-type *Synechococcus elongatus* PCC 7942 strain (ATCC® 33912™). FIG. 5 schematically describes the transformation of a wild-type *Synechococcus elongatus* PCC 7942 strain using the SyneBrick vectors having different promoters. Since the wild-type strain has a neutral site (NSI) which usually does not function, the spectinomycin-resistant gene, the repressor, the promoter and the GFP gene were inserted directly onto the *Synechococcus elongatus* PCC 7942 genome based on the complementary matching of NSIa (SEQ ID NO 7) and NSIb (SEQ ID NO 8) sequences of SyneBrick with the NSI sequence (FIG. 5).

[Example 3] Testing of SyneBrick Vector for Gene Expression in *Synechococcus elongatus* PCC 7942

It was tested whether the constructed 5 SyneBrick vectors are appropriate for gene expression in *Synechococcus elongatus* PCC 7942. First, the expression of the GFP gene of the newly constructed SyneBrick vectors was observed by confocal microscopy.

Figure 6:
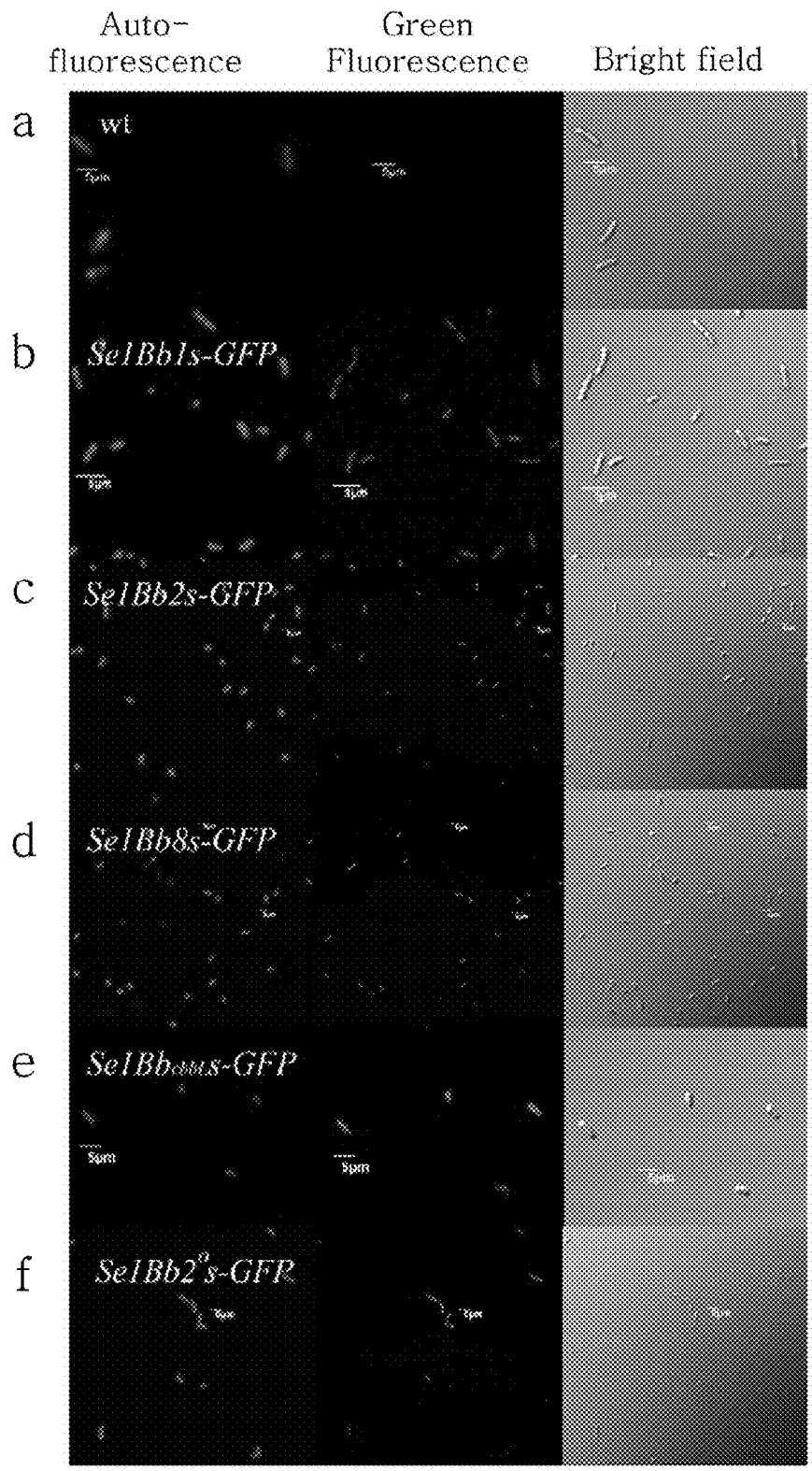
FIG. 6 shows confocal microscopic images of green fluorescent protein (GFP) fluorescence by constructed strains.
Figure 7A:
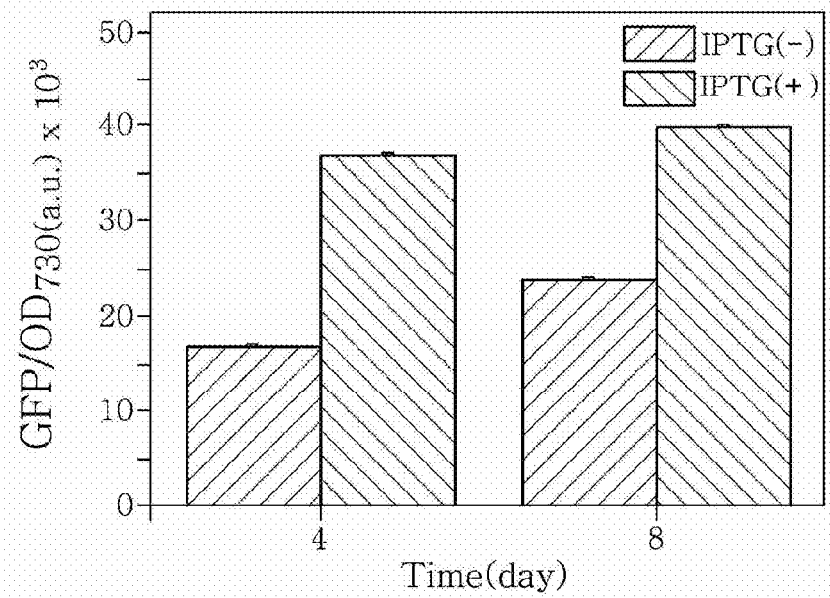
FIG. 7 shows a result of measuring GFP fluorescence by SyneBrick vectors in the presence or absence of an inducer.
Figure 7B:
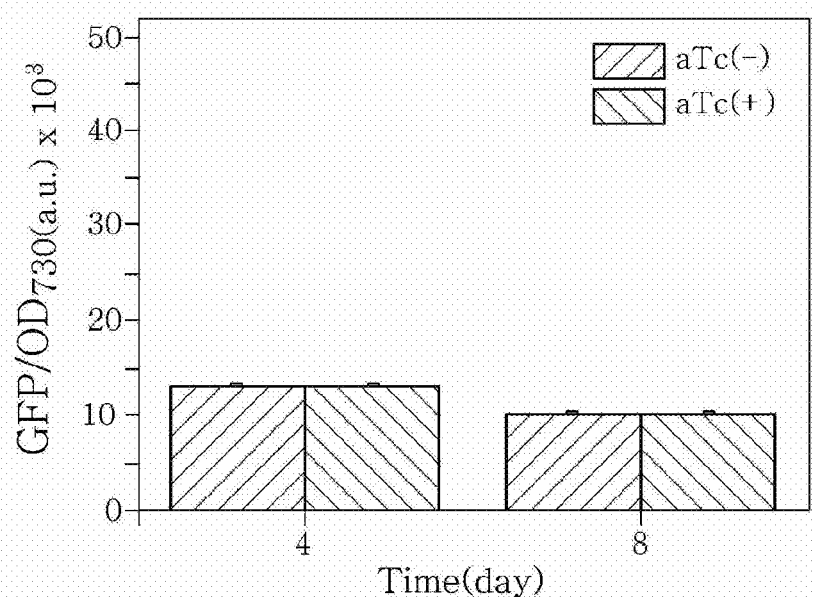
Figure 7C:
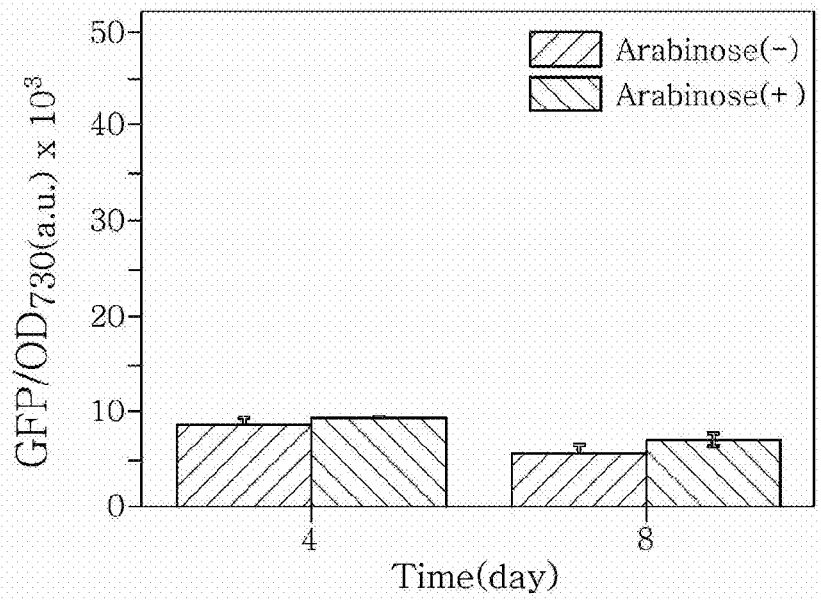
Figure 7D:
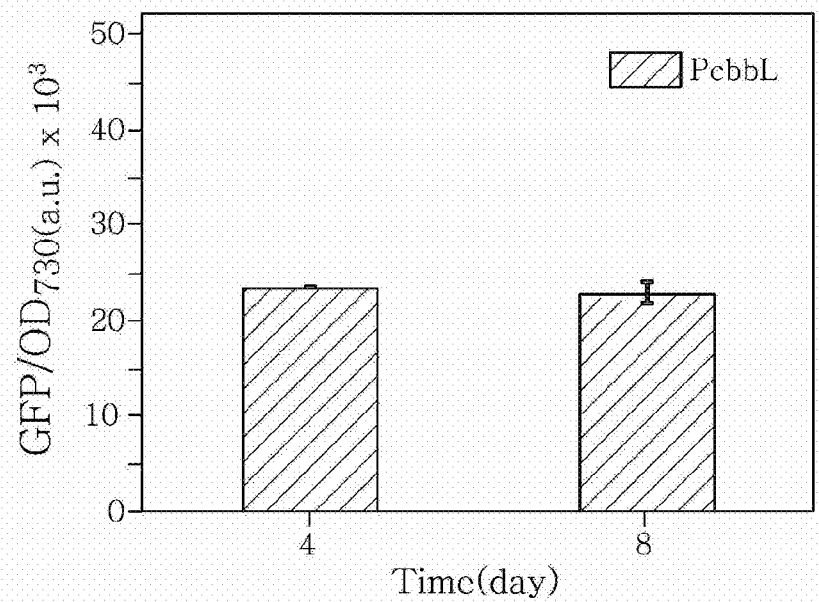
Figure 7E:
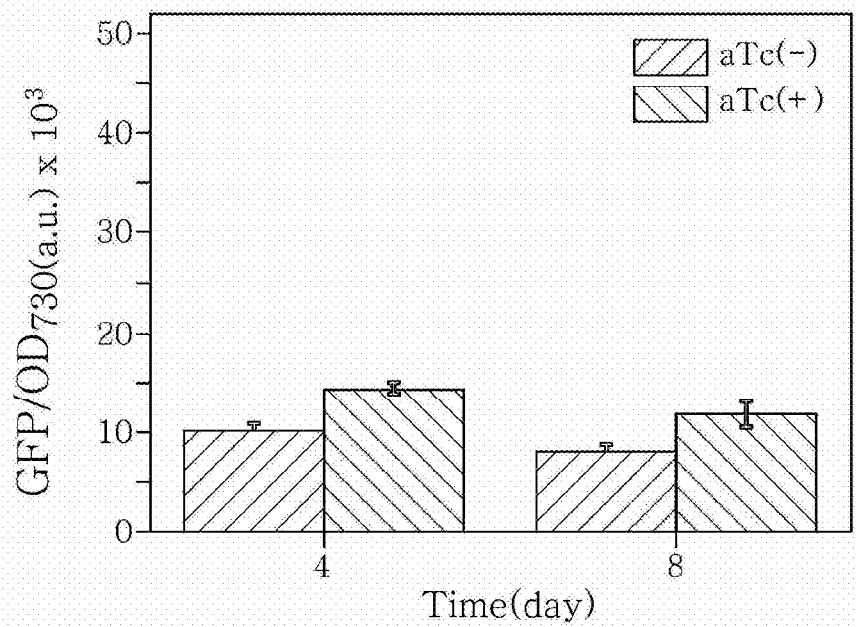

Referring to FIG. 6, the left lane shows original red autofluorescence characteristic of the strain and the middle lane shows green fluorescence originating from the added GFP gene. The topmost row shows images of the wild-type *Synechococcus elongatus* PCC 7942 strain and green fluorescence is not observed in the middle image. Olympus Fluoview FV1000 was used for the confocal microscopy. The green fluorescence images were obtained using 488 nm/500-530 nm (excitation/emission) lasers and the red fluorescence images were obtained using 543 nm/570-640 nm (excitation/emission) lasers. The strain was induced using an inducer and the images were obtained after reaching an exponential phase.

Also, the intensity of fluorescence by the GFP located downstream of the promoter was measured using an automatic microplate reader (Tecan Infinite M200 pro, Tecan Group Ltd., Switzerland) at wavelengths of 485/535 nm. The measured fluorescence intensity was divided by the optical density at 730 nm. The GFP fluorescence intensity per unit cells was determined on days 4 and 8 after culturing.

The culturing condition was as follows. 100 mL of BG-11 medium (UTEX The Culture Collection of Algae at The University of Texas at Austin) with a composition described in Table 1 was added to a 250-mL Erlenmeyer flask and then the mutant strain transformed with each of the 5 SyneBrick vectors was added after diluting to O.D. 0.6.

TABLE 1

| | Ingredients | Contents | Stock solution conc. | Final conc. |
|---|---|---|---|---|
| 1 | NaNO$_3$ (Fisher BP360-500) | 10 mL/L | 30 g/200 mL dH$_2$O | 17.6 mM |
| 2 | K$_2$HPO$_4$ (Sigma P 3786) | 10 mL/L | 0.8 g/200 mL dH$_2$O | 0.23 mM |
| 3 | MgSO$_4$•7H$_2$O (Sigma 230391) | 10 mL/L | 1.5 g/200 mL dH$_2$O | 0.3 mM |
| 4 | CaCl$_2$•2H$_2$O (Sigma C-3881) | 10 mL/L | 0.72 g/200 mL dH$_2$O | 0.24 mM |
| 5 | Citric acid•H$_2$O (Fisher A 104) | 10 mL/L | 0.12 g/200 mL dH$_2$O | 0.031 mM |
| 6 | Ferric ammonium citrate | 10 mL/L | 0.12 g/200 mL dH$_2$O | 0.021 mM |
| 7 | Na$_2$EDTA•2H$_2$O (Sigma ED255) | 10 mL/L | 0.02 g/200 mL dH$_2$O | 0.0027 mM |
| 8 | Na$_2$CO$_3$ (Baker 3604) | 10 mL/L | 0.4 g/200 mL dH$_2$O | 0.19 mM |
| 9 | BG-11 trace metals solution | 1 mL/L | | |
| 10 | Sodium thiosulfate pentahydrate (agar media only, sterile; Baker 3946) | 1 mL/L | 49.8 g/200 mL dH$_2$O | 1 mM |

Also, the strain was cultured at 30 and 130 rpm while supplying 5% CO$_2$ continuously after adding 10 μg/mL of spectinomycin and an inducer required for GFP expression (0.1 mM IPTG, 200 nM aTC, 1 mM arabinose).

On days 4 and 8 after the culturing was initiated, the growing cells were added to a 96-well plate (flat bottom 96-well solid black plate, Corning, USA) with 200 μL per each, and GFP fluorescence was measured using an automatic microplate reader.

From FIG. 7, A, it can be seen that the Se1Bb1s-GFP strain induced with 0.1 mM IPTG showed 2.2-fold increased GFP fluorescence on day 4 and 1.7-fold increased GFP fluorescence on day 8, as compared to when it was not induced.

Referring to FIG. 7, D, the Se1BbcbbLs-GFP strain showed consistent GFP fluorescence without recurring induction. The fluorescence intensity was similar to that of Se1Bb1s-GFP before induction.

From FIGS. 7, B and C, it can be seen that the fluorescence by the Se1Bb2s-GFP and Se1Bb8s-GFP strains is not regulated by the inducer. Therefore, the same experiment was conducted after preparing a new strain using pSe1Bb2$^O$s-GFP. In the presence of the inducer, the fluorescence intensity increased 1.4-fold on day 4 and 1.5-fold on day 8 (FIG. 7, E).

The invention claimed is:

1. An expression vector which is operable in cyanobacteria comprising, sequentially:
   a pUC replication origin as a replication origin;
   a spectinomycin-resistant gene as a selection marker; and
   a promoter selected from a group consisting of a trc promoter, a tetA promoter or a modified tetA promoter, a BAD promoter and a cbbL promoter,
   wherein the modified tetA promoter comprises a sequence of SEQ ID NO 6.

2. The vector according to claim 1, wherein the vector further comprises a repressor selected from a group consisting of a lad repressor, a tetR repressor and an AraC repressor upstream of the promoter.

3. The vector according to claim 1, wherein the vector further comprises a green fluorescent protein (GFP) gene downstream of the promoter.

4. The vector according to claim 1, wherein the vector further comprises a neutral site (NSI) comprising the neutral site comprising:
   NSIa comprising a sequence of SEQ ID NO 7; and
   NSIb comprising a sequence of SEQ ID NO 8.

5. The vector according to claim 1, wherein the vector further comprises a BglII site and a BamHI site as restriction enzyme sites.

6. The vector according to claim 5, wherein the vector further comprises a target DNA sequence which encodes a target protein desired to be overexpressed.

7. The vector according to claim 6, wherein the BglII site and the BamHI site are located on both sides of the target DNA sequence.

8. The vector according to claim 7, wherein the target DNA sequence encodes two or more proteins.

9. The vector according to claim 8, wherein the target DNA sequence is included in the vector by complementary binding between the BglII site of the upstream side of a first portion of the target DNA sequence and the BamHI site of the downstream side of a second portion of the target DNA sequence.

10. The vector according to claim 1, wherein the vector is
    a pSe1Bb1s-GFP vector comprising a lad repressor and a trc promoter;
    a pSe1Bb2s-GFP vector comprising a tetR repressor and a tetA promoter;
    a pSe1Bb8s-GFP vector comprising an AraC repressor and a BAD promoter;
    a pSe1Bb$_{cbbL}$s-GFP vector comprising a cbbL promoter; or
    a pSe1Bb2$^O$s-GFP vector comprising a tetR repressor and a modified tetA promoter comprising a sequence of SEQ ID NO 6.

11. The vector according to claim 10, wherein the vector comprises a sequence of SEQ ID NO 1; SEQ ID NO 2; SEQ ID NO 3; SEQ ID NO 4; or SEQ ID NO 5.

12. A host cell transformed with the vector according to claim 1.

13. The host cell according to claim 12, wherein the host cell is cyanobacterium.

14. The host cell according to claim 13, wherein the cyanobacterium is *Synechococcus elongatus*.

15. A host cell transformed with the vector according to claim 10.

16. A host cell transformed with the vector according to claim 11.

17. Transformed *Synechococcus* elongates PCC 7942 in which the vector according to claim 4 is inserted onto the genome of *Synechococcus* elongates PCC 7942 via the neutral site between NSIa and NSIb.

* * * * *

SEQUENCE LISTING

<160> NUMBER OF SEQ ID NOS: 10

<210> SEQ ID NO 1
<211> LENGTH: 5907
<212> TYPE: DNA
<213> ORGANISM: Artificial Sequence
<220> FEATURE:
<223> OTHER INFORMATION: pSe1Bb1s-GFP vector
<220> FEATURE:
<221> NAME/KEY: rep_origin
<222> LOCATION: (58)..(673)
<223> OTHER INFORMATION: pUC origin
<220> FEATURE:
<221> NAME/KEY: unsure
<222> LOCATION: (745)..(1543)
<223> OTHER INFORMATION: NSIa
<220> FEATURE:
<221> NAME/KEY: gene
<222> LOCATION: (1684)..(2694)
<223> OTHER INFORMATION: Spectinomycin resistance gene
<220> FEATURE:
<221> NAME/KEY: gene
<222> LOCATION: (2790)..(3881)
<223> OTHER INFORMATION: LacI repressor
<220> FEATURE:
<221> NAME/KEY: promoter
<222> LOCATION: (3938)..(4172)
<223> OTHER INFORMATION: trc promoter
<220> FEATURE:
<221> NAME/KEY: gene
<222> LOCATION: (4187)..(4923)
<223> OTHER INFORMATION: green fluorescent protein
<220> FEATURE:
<221> NAME/KEY: unsure
<222> LOCATION: (5132)..(5907)
<223> OTHER INFORMATION: NSIb

<400> SEQUENCE: 1

| | | | | | |
|---|---|---|---|---|---|
| gataatctca | tgaccaaaat | cccttaacgt | gagttttcgt | tccactgagc | gtcagacccc | 60 |
| gtagaaaaga | tcaaaggatc | ttcttgagat | cctttttttc | tgcgcgtaat | ctgctgcttg | 120 |
| caaacaaaaa | aaccaccgct | accagcggtg | gtttgtttgc | cggatcaaga | gctaccaact | 180 |
| cttttccga | aggtaactgg | cttcagcaga | gcgcagatac | caaatactgt | tcttctagtg | 240 |
| tagccgtagt | taggccacca | cttcaagaac | tctgtagcac | cgcctacata | cctcgctctg | 300 |
| ctaatcctgt | taccagtggc | tgctgccagt | ggcgataagt | cgtgtcttac | cgggttggac | 360 |
| tcaagacgat | agttaccgga | taaggcgcag | cggtcgggct | gaacggggggg | ttcgtgcaca | 420 |
| cagcccagct | tggagcgaac | gacctacacc | gaactgagat | acctacagcg | tgagctatga | 480 |
| gaaagcgcca | cgcttcccga | agggagaaag | gcggacaggt | atccggtaag | cggcagggtc | 540 |
| ggaacaggag | agcgcacgag | ggagcttcca | gggggaaacg | cctggtatct | ttatagtcct | 600 |
| gtcgggtttc | gccacctctg | acttgagcgt | cgatttttgt | gatgctcgtc | aggggggcgg | 660 |
| agcctatgga | aaaacgccag | caacgcggcc | tttttacggt | tcctggcctt | ttgctggcct | 720 |
| tttgctcaca | tgtgtgctgg | gccccaatgc | cttctccaag | ggcggcattc | ccctgactgt | 780 |
| tgaaggcgtt | gccaatatca | agattgctgg | ggaagaaccg | accatccaca | acgcgatcga | 840 |
| gcggctgctt | ggcaaaaacc | gtaaggaaat | cgagcaaatt | gccaaggaga | ccctcgaagg | 900 |
| caacttgcgt | ggtgttttag | ccagcctcac | gccggagcag | atcaacgagg | acaaaattgc | 960 |
| cttgccaaa | agtctgctgg | aagaggcgga | ggatgacctt | gagcagctgg | gtcaagtcct | 1020 |
| cgatacgctg | caagtccaga | acatttccga | tgaggtcggt | tatctctcgg | ctagtggacg | 1080 |
| caagcagcgg | gctgatctgc | agcgagatgc | ccgaattgct | gaagccgatg | cccaggctgc | 1140 |
| ctctgcgatc | caaacggccg | aaaatgacaa | gatcacggcc | ctgcgtcgga | tcgatcgcga | 1200 |

```
tgtagcgatc gcccaagccg aggccgagcg ccggattcag gatgcgttga cgcggcgcga    1260
agcggtggtg gccgaagctg aagcggacat tgctaccgaa gtcgctcgta gccaagcaga    1320
actccctgtg cagcaggagc ggatcaaaca ggtgcagcag caacttcaag ccgatgtgat    1380
cgccccagct gaggcagctt gtaaacgggc gatcgcggaa gcgcggggg ccgccgcccg     1440 tatcgtcgaa gatggaaaag ctcaagcgga agggacccaa cggctggcgg aggcttggca    1500
gaccgctggt gctaatgccc gcgacatctt cctgctccag aagtctagac cagccaggac    1560
agaaatgcct cgacttcgct gctacccaag gttgccgggt gacgcacacc gtggaaacgg    1620
atgaaggcac gaacccagtg gacataagcc tgttcggttc gtaagctgta atgcaagtag    1680
cgtatgcgct cacgcaactg gtccagaacc ttgaccgaac gcagcggtgg taacggcgca    1740
gtggcggttt tcatggcttg ttatgactgt ttttttgggg tacagtctat gcctcgggca    1800
tccaagcagc aagcgcgtta cgccgtgggt cgatgtttga tgttatggag cagcaacgat    1860
gttacgcagc agggcagtcg ccctaaaaca aagttaaaca ttatgaggga agcggtgatc    1920
gccgaagtat cgactcaact atcagaggta gttggcgtca tcgagcgcca tctcgaaccg    1980
acgttgctgg ccgtacattt gtacggctcc gcagtggatg gcggcctgaa gccacacagt    2040
gatattgatt tgctggttac ggtgaccgta aggcttgatg aaacaacgcg gcgagctttg    2100
atcaacgacc ttttggaaac ttcggcttcc cctggagaga gcgagattct ccgcgctgta    2160
gaagtcacca ttgttgtgca cgacgacatc attccgtggc gttatccagc taagcgcgaa    2220
ctgcaatttg gagaatggca gcgcaatgac attcttgctg gtatcttcga gccagccacg    2280
atcgacattg atctggctat cttgctgaca aaagcaagag aacatagcgt tgccttggta    2340
ggtccagcgg cggaggaact ctttgatccg gttcctgaac aggatctatt tgaggcgcta    2400
aatgaaacct taacgctatg gaactcgccg cccgactggg ctggcgatga gcgaaatgta    2460
gtgcttacgt tgtcccgcat ttggtacagc gcagtaaccg gcaaaatcgc gccgaaggat    2520
gtcgctgccg actgggcaat ggagcgcctg ccggcccagt atcagcccgt catacttgaa    2580
gctagacagg cttatcttgg acaagaagaa gatcgcttgg cctcgcgcgc agatcagttg    2640
gaagaatttg tccactacgt gaaaggcgag atcaccaagg tagtcggcaa ataacctcat    2700
tttcgccaga tatcgacgtc gacaccatcg aatggtgcaa aaccctttcgc ggtatggcat    2760 gatagcgccc ggaagagagt caattcaggg tggtgaatgt gaaaccagta acgttatacg    2820
atgtcgcaga gtatgccggt gtctcttatc agaccgtttc ccgcgtggtg aaccaggcca    2880
gccacgtttc tgcgaaaacg cgggaaaaag tggaagcggc gatggcggag ctgaattaca    2940
ttcccaaccg cgtggcacaa caactggcgg gcaaacagtc gttgctgatt ggcgttgcca    3000
cctccagtct ggccctgcac gcgccgtcgc aaattgtcgc ggcgattaaa tctcgcgccg    3060
atcaactggg tgccagcgtg gtggtgtcga tggtagaacg aagcggcgtc gaagcctgta    3120
aagcggcggt gcacaatctt ctcgcgcaac gcgtcagtgg gctgatcatt aactatccgc    3180
tggatgacca ggatgccatt gctgtggaag ctgcctgcac taatgttccg gcgttatttc    3240
ttgatgtctc tgaccagaca cccatcaaca gtattatttt ctcccatgaa gacggtacgc    3300
gactgggcgt ggagcatctg gtcgcattgg gtcaccagca atcgcgctg ttagcgggcc    3360 cattaagttc tgtctcggcg cgtctgcgtc tggctggctg gcataaatat ctcactcgca    3420
atcaaattca gccgatagcg gaacgggaag gcgactggag tgccatgtcc ggttttcaac    3480
aaaccatgca aatgctgaat gagggcatcg ttcccactgc gatgctggtt gccaacgatc    3540
```

-continued

```
agatggcgct gggcgcaatg cgcgccatta ccgagtccgg gctgcgcgtt ggtgcggata    3600
tctcggtagt gggatacgac gataccgaag acagctcatg ttatatcccg ccgttaacca    3660
ccatcaaaca ggattttcgc ctgctggggc aaaccagcgt ggaccgcttg ctgcaactct    3720
ctcagggcca ggcggtgaag ggcaatcagc tgttgcccgt ctcactggtg aaagaaaaa     3780 ccaccctggc gcccaatacg caaaccgcct ctccccgcgc gttggccgat tcattaatgc    3840
agctggcacg acaggtttcc cgactggaaa gcgggcagtg agcgcaacgc aattaatgta    3900
agttagcgcg aattgatctg gtttgacagc ttatcatcga ctgcacggtg caccaatgct    3960
tctggcgtca ggcagccatc ggaagctgtg gtatggctgt gcaggtcgta atcactgca     4020 taattcgtgt cgctcaaggc gcactcccgt tctggataat gttttttgcg ccgacatcat    4080
aacggttctg gcaaatattc tgaaatgagc tgttgacaat taatcatccg gctcgtataa    4140
tgtgtggaat tgtgagcgga taacaatttc agaattcaaa agatctttta agaaggagat    4200
atacatatga gtaaaggaga agaacttttc actggagttg tcccaattct tgttgaatta    4260
gatggtgatg ttaatgggca caaattttct gtcagtggag agggtgaagg tgatgcaaca    4320
tacggaaaac ttacccttaa atttatttgc actactggaa aactacctgt tccgtggcca    4380
acacttgtca ctactttctc ttatggtgtt caatgctttt cccgttatcc ggatcacatg    4440
aaacggcatg acttttcaa gagtgccatg cccgaaggtt atgtacagga acgcactata    4500
tctttcaaag atgacgggaa ctacaagacg cgtgctgaag tcaagtttga aggtgatacc    4560
cttgttaatc gtatcgagtt aaaaggtatt gattttaaag aagatggaaa cattctcgga    4620
cacaaactgg agtacaacta taactcacac aatgtataca tcacggcaga caacaaaag    4680 aatggaatca aagctaactt caaaattcgc cacaacattg aagatggctc cgttcaacta    4740
gcagaccatt atcaacaaaa tactccaatt ggcgatggcc ctgtcctttt accagacaac    4800
cattacctgt ccacacaatc tgccctttcg aaagatccca acgaaaagcg tgaccacatg    4860
gtccttcttg agtttgtaac tgctgctggg attacacatg gcatggatga gctctacaaa    4920
taaggatcca aactcgagta aggatctcca ggcatcaaat aaaacgaaag gctcagtcga    4980
aagactgggc ctttcgtttt atctgttgtt tgtcggtgaa cgctctctac tagagtcaca    5040
ctggctcacc ttcgggtggg cctttctgcg tttataccta gggcgttcgg ctgcggcgag    5100
cggtatcagc tcactcaaag gcggtaatac gtccctgctc gtcacgcttt caggcaccgt    5160
gccagatatc gacgtggagt cgatcactgt gattggcgaa ggggaaggca gcgctaccca    5220
aatcgctagc ttgctggaga agctgaaaca aaccacgggc attgatctgg cgaaatccct    5280
accgggtcaa tccgactcgc ccgctgcgaa gtcctaagag atagcgatgt gaccgcgatc    5340
gcttgtcaag aatcccagtg atcccgaacc ataggaaggc aagctcaatg cttgcctcgt    5400
cttgaggact atctagatgt ctgtggaacg cacatttatt gccatcaagc ccgatggcgt    5460
tcagcggggt ttggtcggta cgatcatcgg ccgctttgag caaaaaggct tcaaactggt    5520
gggcctaaag cagctgaagc ccagtcgcga gctggccgaa cagcactatg ctgtccaccg    5580
cgagcgcccc ttcttcaatg gcctcgtcga gttcatcacc tctgggccga tcgtggcgat    5640
cgtcttggaa ggcgaaggcg ttgtggcggc tgctcgcaag ttgatcggcg ctaccaatcc    5700
gctgacggca gaaccgggca ccatccgtgg tgattttggt gtcaatattg gccgcaacat    5760
catccatggc tcggatgcaa tcgaaacagc acaacaggaa attgctctct ggtttagccc    5820
agcagagcta agtgattgga cccccacgat tcaccctggg ctgtacgaat aaggtctgca    5880
ttccttcaga gagacattgc catgccc                                         5907
```

<210> SEQ ID NO 2
<211> LENGTH: 5156
<212> TYPE: DNA
<213> ORGANISM: Artificial Sequence
<220> FEATURE:
<223> OTHER INFORMATION: pSe1Bb2s-GFP vector
<220> FEATURE:
<221> NAME/KEY: rep_origin
<222> LOCATION: (58)..(673)
<223> OTHER INFORMATION: pUC origin
<220> FEATURE:
<221> NAME/KEY: unsure
<222> LOCATION: (745)..(1543)
<223> OTHER INFORMATION: NSIa
<220> FEATURE:
<221> NAME/KEY: gene
<222> LOCATION: (1684)..(2694)
<223> OTHER INFORMATION: Spectinomycin resistance gene
<220> FEATURE:
<221> NAME/KEY: gene
<222> LOCATION: (2721)..(3347)
<223> OTHER INFORMATION: tetR repressor
<220> FEATURE:
<221> NAME/KEY: promoter
<222> LOCATION: (3348)..(3420)
<223> OTHER INFORMATION: tetA promoter
<220> FEATURE:
<221> NAME/KEY: gene
<222> LOCATION: (3436)..(4172)
<223> OTHER INFORMATION: green fluorescent protein
<220> FEATURE:
<221> NAME/KEY: unsure
<222> LOCATION: (4381)..(5156)
<223> OTHER INFORMATION: NSIb

<400> SEQUENCE: 2

```
gataatctca tgaccaaaat cccttaacgt gagttttcgt tccactgagc gtcagacccc    60
gtagaaaaga tcaaaggatc ttcttgagat cctttttttc tgcgcgtaat ctgctgcttg   120
caaacaaaaa aaccaccgct accagcggtg gtttgtttgc cggatcaaga gctaccaact   180
ctttttccga aggtaactgg cttcagcaga gcgcagatac caaatactgt tcttctagtg   240
tagccgtagt taggccacca cttcaagaac tctgtagcac cgcctacata cctcgctctg   300
ctaatcctgt taccagtggc tgctgccagt ggcgataagt cgtgtcttac cgggttggac   360
tcaagacgat agttaccgga taaggcgcag cggtcgggct gaacggggggg ttcgtgcaca   420 cagcccagct tggagcgaac gacctacacc gaactgagat acctacagcg tgagctatga   480
gaaagcgcca cgcttcccga agggagaaag gcggacaggt atccggtaag cggcagggtc   540
ggaacaggag agcgcacgag ggagcttcca gggggaaacg cctggtatct ttatagtcct   600
gtcgggtttc gccacctctg acttgagcgt cgatttttgt gatgctcgtc aggggggcgg   660
agcctatgga aaaacgccag caacgcggcc ttttacggtt cctggccttt tgctggcctt   720
tttgctcaca tgtgtgctgg gccccaatgc cttctccaag ggcggcattc ccctgactgt   780
tgaaggcgtt gccaatatca agattgctgg ggaagaaccg accatccaca acgcgatcga   840
gcggctgctt ggcaaaaacc gtaaggaaat cgagcaaatt gccaaggaga ccctcgaagg   900
caacttgcgt ggtgttttag ccagcctcac gccggagcag atcaacgagg acaaaattgc   960 cttgccaaa agtctgctgg aagaggcgga ggatgacctt gagcagctgg gtcaagtcct  1020
cgatacgctg caagtccaga acatttccga tgaggtcggt tatctctcgg ctagtggacg  1080
caagcagcgg gctgatctgc agcgagatgc ccgaattgct gaagccgatg cccaggctgc  1140
ctctgcgatc caaacggccg aaaatgacaa gatcacggcc ctgcgtcgga tcgatcgcga  1200
```

```
tgtagcgatc gcccaagccg aggccgagcg ccggattcag gatgcgttga cgcggcgcga    1260
agcggtggtg gccgaagctg aagcggacat tgctaccgaa gtcgctcgta gccaagcaga    1320
actccctgtg cagcaggagc ggatcaaaca ggtgcagcag caacttcaag ccgatgtgat    1380
cgccccagct gaggcagctt gtaaacgggc gatcgcggaa gcgcgggggg ccgccgcccg    1440
tatcgtcgaa gatggaaaag ctcaagcgga agggacccaa cggctggcgg aggcttggca    1500
gaccgctggt gctaatgccc gcgacatctt cctgctccag aagtctagac cagccaggac    1560
agaaatgcct cgacttcgct gctacccaag gttgccgggt gacgcacacc gtggaaacgg    1620
atgaaggcac gaacccagtg gacataagcc tgttcggttc gtaagctgta atgcaagtag    1680
cgtatgcgct cacgcaactg gtccagaacc ttgaccgaac gcagcggtgg taacggcgca    1740
gtggcggttt tcatggcttg ttatgactgt ttttttgggg tacagtctat gcctcgggca    1800
tccaagcagc aagcgcgtta cgccgtgggt cgatgtttga tgttatggag cagcaacgat    1860
gttacgcagc agggcagtcg ccctaaaaca aagttaaaca ttatgaggga agcggtgatc    1920
gccgaagtat cgactcaact atcagaggta gttggcgtca tcgagcgcca tctcgaaccg    1980
acgttgctgg ccgtacattt gtacggctcc gcagtggatg gcggcctgaa gccacacagt    2040
gatattgatt tgctggttac ggtgaccgta aggcttgatg aaacaacgcg gcgagctttg    2100
atcaacgacc ttttggaaac ttcggcttcc cctggagaga gcgagattct ccgcgctgta    2160
gaagtcacca ttgttgtgca cgacgacatc attccgtggc gttatccagc taagcgcgaa    2220
ctgcaatttg gagaatggca gcgcaatgac attcttgctg gtatcttcga gccagccacg    2280
atcgacattg atctggctat cttgctgaca aaagcaagag aacatagcgt tgccttggta    2340
ggtccagcgg cggaggaact ctttgatccg gttcctgaac aggatctatt tgaggcgcta    2400
aatgaaacct aacgctatg gaactcgccg cccgactggg ctggcgatga gcgaaatgta    2460
gtgcttacgt tgtcccgcat ttggtacagc gcagtaaccg gcaaaatcgc gccgaaggat    2520
gtcgctgccg actgggcaat ggagcgcctg ccggcccagt atcagcccgt catacttgaa    2580
gctagacagg cttatcttgg acaagaagaa gatcgcttgg cctcgcgcgc agatcagttg    2640
gaagaatttg tccactacgt gaaaggcgag atcaccaagg tagtcggcaa ataacctcat    2700
tttcgccaga tatcgacgtc ttaagaccca cttttcacatt taagttgttt ttctaatccg    2760
catatgatca attcaaggcc gaataagaag gctggctctg caccttggtg atcaaataat    2820
tcgatagctt gtcgtaataa tggcggcata ctatcagtag taggtgtttc ccttcttct    2880
ttagcgactt gatgctcttg atcttccaat acgcaaccta aagtaaaatg ccccacagcg    2940
ctgagtgcat ataatgcatt ctctagtgaa aaaccttgtt ggcataaaaa ggctaattga    3000
ttttcgagag tttcatactg ttttttctgta ggccgtgtac ctaaatgtac ttttgctcca    3060
tcgcgatgac ttagtaaagc acatctaaaa cttttagcgt tattacgtaa aaaatcttgc    3120
cagctttccc cttctaaagg gcaaaagtga gtatggtgcc tatctaacat ctcaatggct    3180
aaggcgtcga gcaaagcccg cttattttt acatgccaat acaatgtagg ctgctctaca    3240
cctagcttct gggcgagttt acgggttgtt aaaccttcga ttccgacctc attaagcagc    3300
tctaatgcgc tgttaatcac tttacttta tctaatctag acatcattaa ttcctaattt    3360
ttgttgacac tctatcgttg atagagttat tttaccactc cctatcagtg atagagaaaa    3420
gaattcaaaa gatcttttaa gaaggagata tacatatgag taaaggagaa gaacttttca    3480
ctggagttgt cccaattctt gttgaattag atggtgatgt taatgggcac aaattttctg    3540
tcagtggaga gggtgaaggt gatgcaacat acggaaaact tacccttaaa tttatttgca    3600
```

-continued

```
ctactggaaa actacctgtt ccgtggccaa cacttgtcac tactttctct tatggtgttc   3660
aatgcttttc ccgttatccg gatcacatga aacggcatga cttttcaag agtgccatgc    3720
ccgaaggtta tgtacaggaa cgcactatat ctttcaaaga tgacgggaac tacaagacgc   3780
gtgctgaagt caagtttgaa ggtgataccc ttgttaatcg tatcgagtta aaaggtattg   3840
atttaaaga agatggaaac attctcggac acaaactgga gtacaactat aactcacaca   3900
atgtatacat cacggcagac aaacaaaaga atggaatcaa agctaacttc aaaattcgcc   3960
acaacattga agatggctcc gttcaactag cagaccatta tcaacaaaat actccaattg   4020
gcgatggccc tgtccttta ccagacaacc attacctgtc cacacaatct gccctttcga   4080
aagatcccaa cgaaaagcgt gaccacatgg tccttcttga gtttgtaact gctgctggga   4140
ttacacatgg catggatgag ctctacaaat aaggatccaa actcgagtaa ggatctccag   4200
gcatcaaata aaacgaaagg ctcagtcgaa agactgggcc tttcgtttta tctgttgttt   4260
gtcggtgaac gctctctact agagtcacac tggctcacct tcgggtgggc ctttctgcgt   4320
ttataccag ggcgttcggc tgcggcgagc ggtatcagct cactcaaagg cggtaatacg   4380
tccctgctcg tcacgctttc aggcaccgtg ccagatatcg acgtggagtc gatcactgtg   4440
attggcgaag gggaaggcag cgctacccaa atcgctagct tgctggagaa gctgaaacaa   4500
accacgggca ttgatctggc gaaatcccta ccgggtcaat ccgactcgcc cgctgcgaag   4560
tcctaagaga tagcgatgtg accgcgatcg cttgtcaaga atcccagtga tcccgaacca   4620
taggaaggca agctcaatgc ttgcctcgtc ttgaggacta tctagatgtc tgtggaacgc   4680
acatttattg ccatcaagcc cgatggcgtt cagcggggtt tggtcggtac gatcatcggc   4740
cgctttgagc aaaaggctt caaactggtg ggcctaaagc agctgaagcc cagtcgcgag   4800
ctggccgaac agcactatgc tgtccaccgc gagcgcccct tcttcaatgg cctcgtcgag   4860
ttcatcacct ctgggccgat cgtggcgatc gtcttggaag gcgaaggcgt tgtggcggct   4920
gctcgcaagt tgatcggcgc taccaatccg ctgacggcag aaccgggcac catccgtggt   4980
gattttggtg tcaatattgg ccgcaacatc atccatggct cggatgcaat cgaaacagca   5040
caacaggaaa ttgctctctg gtttagccca gcagagctaa gtgattggac ccccacgatt   5100
caaccctggc tgtacgaata aggtctgcat tccttcagag agacattgcc atgccc       5156
```

<210> SEQ ID NO 3
<211> LENGTH: 5660
<212> TYPE: DNA
<213> ORGANISM: Artificial Sequence
<220> FEATURE:
<223> OTHER INFORMATION: pSe1Bb8s-GFP vector
<220> FEATURE:
<221> NAME/KEY: rep_origin
<222> LOCATION: (58)..(673)
<223> OTHER INFORMATION: pUC origin
<220> FEATURE:
<221> NAME/KEY: unsure
<222> LOCATION: (745)..(1543)
<223> OTHER INFORMATION: NSIa
<220> FEATURE:
<221> NAME/KEY: gene
<222> LOCATION: (1684)..(2694)
<223> OTHER INFORMATION: Spectinomycin resistance gene
<220> FEATURE:
<221> NAME/KEY: gene
<222> LOCATION: (2721)..(3599)
<223> OTHER INFORMATION: Ara C repressor
<220> FEATURE:
<221> NAME/KEY: promoter
<222> LOCATION: (3875)..(3902)

```
<223> OTHER INFORMATION: BAD promoter
<220> FEATURE:
<221> NAME/KEY: gene
<222> LOCATION: (3940)..(4676)
<223> OTHER INFORMATION: green fluorescent protein
<220> FEATURE:
<221> NAME/KEY: unsure
<222> LOCATION: (4885)..(5660)
<223> OTHER INFORMATION: NSIb

<400> SEQUENCE: 3
```

| | | | | | |
|---|---|---|---|---|---|
| gataatctca | tgaccaaaat | cccttaacgt | gagttttcgt | tccactgagc | gtcagacccc | 60 |
| gtagaaaaga | tcaaaggatc | ttcttgagat | cctttttttc | tgcgcgtaat | ctgctgcttg | 120 |
| caaacaaaaa | aaccaccgct | accagcggtg | gtttgtttgc | cggatcaaga | gctaccaact | 180 |
| cttttttccga | aggtaactgg | cttcagcaga | gcgcagatac | caaatactgt | tcttctagtg | 240 |
| tagccgtagt | taggccacca | cttcaagaac | tctgtagcac | cgcctacata | cctcgctctg | 300 |
| ctaatcctgt | taccagtggc | tgctgccagt | ggcgataagt | cgtgtcttac | cgggttggac | 360 |
| tcaagacgat | agttaccgga | taaggcgcag | cggtcgggct | gaacggggg | ttcgtgcaca | 420 |
| cagcccagct | tggagcgaac | gacctacacc | gaactgagat | acctacagcg | tgagctatga | 480 |
| gaaagcgcca | cgcttcccga | agggagaaag | gcggacaggt | atccggtaag | cggcagggtc | 540 |
| ggaacaggag | agcgcacgag | ggagcttcca | gggggaaacg | cctggtatct | ttatagtcct | 600 |
| gtcgggtttc | gccacctctg | acttgagcgt | cgatttttgt | gatgctcgtc | aggggggcgg | 660 |
| agcctatgga | aaaacgccag | caacgcggcc | tttttacggt | tcctggcctt | ttgctggcct | 720 |
| tttgctcaca | tgtgtgctgg | gccccaatgc | cttctccaag | gcggcattc | ccctgactgt | 780 |
| tgaaggcgtt | gccaatatca | agattgctgg | ggaagaaccg | accatccaca | acgcgatcga | 840 |
| gcggctgctt | ggcaaaaacc | gtaaggaaat | cgagcaaatt | gccaaggaga | ccctcgaagg | 900 |
| caacttgcgt | ggtgttttag | ccagcctcac | gccggagcag | atcaacgagg | acaaaattgc | 960 |
| ctttgccaaa | agtctgctgg | aagaggcgga | ggatgacctt | gagcagctgg | gtcaagtcct | 1020 |
| cgatacgctg | caagtccaga | acatttccga | tgaggtcggt | tatctctcgg | ctagtggacg | 1080 |
| caagcagcgg | gctgatctgc | agcgagatgc | ccgaattgct | gaagccgatg | cccaggctgc | 1140 |
| ctctgcgatc | caaacggccg | aaaatgacaa | gatcacggcc | ctgcgtcgga | tcgatcgcga | 1200 |
| tgtagcgatc | gcccaagccg | aggccgagcg | ccggattcag | gatgcgttga | gcgcgcgcga | 1260 |
| agcggtggtg | gccgaagctg | aagcggacat | tgctaccgaa | gtcgctcgta | gccaagcaga | 1320 |
| actccctgtg | cagcaggagc | ggatcaaaca | ggtgcagcag | caacttcaag | ccgatgtgat | 1380 |
| cgccccagct | gaggcagctt | gtaaacgggc | gatcgcggaa | gcgcgggggg | ccgccgcccg | 1440 |
| tatcgtcgaa | gatggaaaag | ctcaagcgga | agggacccaa | cggctggcgg | aggcttggca | 1500 |
| gaccgctggt | gctaatgccc | gcgacatctt | cctgctccag | aagtctagac | cagccaggac | 1560 |
| agaaatgcct | cgacttcgct | gctacccaag | gttgccgggt | gacgcacacc | gtggaaacgg | 1620 |
| atgaaggcac | gaacccagtg | gacataagcc | tgttcggttc | gtaagctgta | atgcaagtag | 1680 |
| cgtatgcgct | cacgcaactg | gtccagaacc | ttgaccgaac | gcagcggtgg | taacggcgca | 1740 |
| gtggcggttt | tcatggcttg | ttatgactgt | ttttttgggg | tacagtctat | gcctcgggca | 1800 |
| tccaagcagc | aagcgcgtta | cgccgtgggt | cgatgtttga | tgttatggag | cagcaacgat | 1860 |
| gttacgcagc | agggcagtcg | ccctaaaaca | aagttaaaca | ttatgaggga | agcggtgatc | 1920 |
| gccgaagtat | cgactcaact | atcagaggta | gttggcgtca | tcgagcgcca | tctcgaaccg | 1980 |
| acgttgctgg | ccgtacattt | gtacggctcc | gcagtggatg | gcggcctgaa | gccacacagt | 2040 |

```
gatattgatt tgctggttac ggtgaccgta aggcttgatg aaacaacgcg gcgagctttg    2100
atcaacgacc ttttggaaac ttcggcttcc cctggagaga gcgagattct ccgcgctgta    2160
gaagtcacca ttgttgtgca cgacgacatc attccgtggc gttatccagc taagcgcgaa    2220
ctgcaatttg gagaatggca gcgcaatgac attcttgctg gtatcttcga gccagccacg    2280
atcgacattg atctggctat cttgctgaca aaagcaagag aacatagcgt tgccttggta    2340
ggtccagcgg cggaggaact ctttgatccg gttcctgaac aggatctatt tgaggcgcta    2400
aatgaaacct taacgctatg gaactcgccg cccgactggg ctggcgatga gcgaaatgta    2460
gtgcttacgt tgtcccgcat ttggtacagc gcagtaaccg gcaaaatcgc gccgaaggat    2520
gtcgctgccg actgggcaat ggagcgcctg ccggcccagt atcagcccgt catacttgaa    2580
gctagacagg cttatcttgg acaagaagaa gatcgcttgg cctcgcgcgc agatcagttg    2640
gaagaatttg tccactacgt gaaaggcgag atcaccaagg tagtcggcaa ataacctcat    2700
tttcgccaga tatcgacgtc ttatgacaac ttgacggcta catcattcac tttttcttca    2760
caaccggcac ggaactcgct cgggctggcc ccggtgcatt ttttaaatac ccgcgagaaa    2820
tagagttgat cgtcaaaacc aacattgcga ccgacggtgg cgataggcat ccgggtggtg    2880
ctcaaaagca gcttcgcctg gctgatacgt tggtcctcgc gccagcttaa gacgctaatc    2940
cctaactgct ggcggaaaag atgtgacaga cgcgacggcg acaagcaaac atgctgtgcg    3000
acgctggcga tatcaaaatt gctgtctgcc aggtgatcgc tgatgtactg acaagcctcg    3060
cgtacccgat tatccatcgg tggatggagc gactcgttaa tcgcttccat gcgccgcagt    3120
aacaattgct caagcagatt tatcgccagc agctccgaat agcgcccttc cccttgcccg    3180
gcgttaatga tttgcccaaa caggtcgctg aaatgcggct ggtgcgcttc atccgggcga    3240
aagaaccccg tattggcaaa tattgacggc cagttaagcc attcatgcca gtaggcgcgc    3300
ggacgaaagt aaacccactg gtgataccat tcgcgagcct ccggatgacg accgtagtga    3360
tgaatctctc ctggcgggaa cagcaaaata tcacccggtc ggcaaacaaa ttctcgtccc    3420
tgatttttca ccaccccctg accgcgaatg gtgagattga gaatataacc tttcattccc    3480
agcggtcggt cgataaaaaa atcgagataa ccgttggcct caatcggcgt taaacccgcc    3540
accagatggg cattaaacga gtatcccggc agcagggat catttgcgc ttcagccata    3600 cttttcatac tcccgccatt cagagaagaa accaattgtc catattgcat cagacattgc    3660
cgtcactgcg tcttttactg gctcttctcg ctaaccaaac cggtaacccc gcttattaaa    3720
agcattctgt aacaaagcgg gaccaaagcc atgacaaaaa cgcgtaacaa aagtgtctat    3780
aatcacggca gaaagtccca cattgattat ttgcacggcg tcacactttg ctatgccata    3840
gcatttttat ccataagatt agcggattct acctgacgct ttttatcgca actctctact    3900
gtttctccat acccgttttt tgggaattc aaaagatctt ttaagaagga gatatacata    3960
tgagtaaagg agaagaactt ttcactggag ttgtcccaat tcttgttgaa ttagatggtg    4020
atgttaatgg gcacaaattt tctgtcagtg gagagggtga aggtgatgca acatacggaa    4080
aacttaccct taaatttatt tgcactactg gaaaactacc tgttccgtgg ccaacacttg    4140
tcactacttt ctcttatggt gttcaatgct ttcccgttta tccggatcac atgaaacggc    4200 atgactttt caagagtgcc atgcccgaag ttatgtaca ggaacgcact atatctttca    4260
aagatgacgg gaactacaag acgcgtgctg aagtcaagtt tgaaggtgat acccttgtta    4320
atcgtatcga gttaaaaggt attgatttta aagaagatgg aaacattctc ggacacaaac    4380
```

```
tggagtacaa ctataactca cacaatgtat acatcacggc agacaaacaa aagaatggaa      4440
tcaaagctaa cttcaaaatt cgccacaaca ttgaagatgg ctccgttcaa ctagcagacc      4500
attatcaaca aaatactcca attggcgatg ccctgtcct tttaccagac aaccattacc       4560
tgtccacaca atctgccctt tcgaaagatc caacgaaaa gcgtgaccac atggtccttc       4620
ttgagtttgt aactgctgct gggattacac atggcatgga tgagctctac aaataaggat     4680
ccaaactcga gtaaggatct ccaggcatca aataaaacga aaggctcagt cgaaagactg     4740
ggcctttcgt tttatctgtt gtttgtcggt gaacgctctc tactagagtc acactggctc     4800
accttcgggt gggcctttct gcgtttatac ctagggcgtt cggctgcggc gagcggtatc     4860
agctcactca aaggcggtaa tacgtccctg ctcgtcacgc tttcaggcac cgtgccagat     4920
atcgacgtgg agtcgatcac tgtgattggc gaagggaag gcagcgctac ccaaatcgct      4980
agcttgctgg agaagctgaa acaaaccacg ggcattgatc tggcgaaatc cctaccgggt     5040
caatccgact cgcccgctgc gaagtcctaa gagatagcga tgtgaccgcg atcgcttgtc     5100
aagaatccca gtgatcccga accataggaa ggcaagctca atgcttgcct cgtcttgagg     5160
actatctaga tgtctgtgga acgcacattt attgccatca agcccgatgg cgttcagcgg     5220
ggtttggtcg gtacgatcat cggccgcttt gagcaaaaag gcttcaaact ggtgggccta     5280
aagcagctga agcccagtcg cgagctggcc gaacagcact atgctgtcca ccgcgagcgc     5340
cccttcttca atggcctcgt cgagttcatc acctctgggc cgatcgtggc gatcgtcttg     5400
gaaggcgaag gcgttgtggc ggctgctcgc aagttgatcg gcgctaccaa tccgctgacg     5460
gcagaaccgg gcaccatccg tggtgatttt ggtgtcaata ttggccgcaa catcatccat     5520
ggctcggatg caatcgaaac agcacaacag gaaattgctc tctggtttag cccagcagag     5580
ctaagtgatt ggaccccac gattcaaccc tggctgtacg aataaggtct gcattccttc      5640
agagagacat tgccatgccc                                                 5660

<210> SEQ ID NO 4
<211> LENGTH: 4670
<212> TYPE: DNA
<213> ORGANISM: Artificial Sequence
<220> FEATURE:
<223> OTHER INFORMATION: pSe1BbcbbLS-GFP vector
<220> FEATURE:
<221> NAME/KEY: rep_origin
<222> LOCATION: (58)..(673)
<223> OTHER INFORMATION: pUC origin
<220> FEATURE:
<221> NAME/KEY: unsure
<222> LOCATION: (745)..(1543)
<223> OTHER INFORMATION: NSIa
<220> FEATURE:
<221> NAME/KEY: gene
<222> LOCATION: (1684)..(2694)
<223> OTHER INFORMATION: Spectinomycin resistance gene
<220> FEATURE:
<221> NAME/KEY: promoter
<222> LOCATION: (2724)..(2934)
<223> OTHER INFORMATION: cbbL promoter
<220> FEATURE:
<221> NAME/KEY: gene
<222> LOCATION: (2950)..(3686)
<223> OTHER INFORMATION: green fluorescent protein
<220> FEATURE:
<221> NAME/KEY: unsure
<222> LOCATION: (3895)..(4670)
<223> OTHER INFORMATION: NSIb

<400> SEQUENCE: 4
gataatctca tgaccaaaat cccttaacgt gagttttcgt tccactgagc gtcagacccc        60
```

```
gtagaaaaga tcaaaggatc ttcttgagat cctttttttc tgcgcgtaat ctgctgcttg    120
caaacaaaaa aaccaccgct accagcggtg gtttgtttgc cggatcaaga gctaccaact    180 cttttttccga aggtaactgg cttcagcaga gcgcagatac caaatactgt tcttctagtg   240
tagccgtagt taggccacca cttcaagaac tctgtagcac cgcctacata cctcgctctg    300
ctaatcctgt taccagtggc tgctgccagt ggcgataagt cgtgtcttac cgggttggac    360
tcaagacgat agttaccgga taaggcgcag cggtcgggct gaacggggggg ttcgtgcaca   420 cagcccagct tggagcgaac gacctacacc gaactgagat acctacagcg tgagctatga    480
gaaagcgcca cgcttcccga agggagaaag gcggacaggt atccggtaag cggcagggtc    540
ggaacaggag agcgcacgag ggagcttcca gggggaaacg cctggtatct ttatagtcct    600
gtcgggtttc gccacctctg acttgagcgt cgattttgt gatgctcgtc aggggggcgg     660
agcctatgga aaaacgccag caacgcggcc ttttacggt tcctggcctt tgctggcct     720 tttgctcaca tgtgtgctgg gccccaatgc cttctccaag gcggcattc ccctgactgt     780 tgaaggcgtt gccaatatca agattgctgg ggaagaaccg accatccaca acgcgatcga    840
gcggctgctt ggcaaaaacc gtaaggaaat cgagcaaatt gccaaggaga ccctcgaagg    900
caacttgcgt ggtgttttag ccagcctcac gccggagcag atcaacgagg acaaaattgc    960
ctttgccaaa agtctgctgg aagaggcgga ggatgacctt gagcagctgg gtcaagtcct   1020
cgatacgctg caagtccaga acatttccga tgaggtcggt tatctctcgg ctagtggacg   1080
caagcagcgg gctgatctgc agcgagatgc ccgaattgct gaagccgatg cccaggctgc   1140
ctctgcgatc caaacggccg aaaatgacaa gatcacggcc ctgcgtcgga tcgatcgcga   1200
tgtagcgatc gcccaagccg aggccgagcg ccggattcag gatgcgttga cgcggcgcga   1260
agcggtggtg gccgaagctg aagcggacat tgctaccgaa gtcgctcgta gccaagcaga   1320
actccctgtg cagcaggagc ggatcaaaca ggtgcagcag caacttcaag ccgatgtgat   1380
cgccccagct gaggcagctt gtaaacgggc gatcgcggaa gcgcgggggg ccgccgcccg   1440
tatcgtcgaa gatggaaaag ctcaagcgga agggacccaa cggctggcgg aggcttggca   1500
gaccgctggt gctaatgccc gcgacatctt cctgctccag aagtctagac cagccaggac   1560
agaaatgcct cgacttcgct gctacccaag gttgccgggt gacgcacacc gtggaaacgg   1620
atgaaggcac gaacccagtg gacataagcc tgttcggttc gtaagctgta atgcaagtag   1680
cgtatgcgct cacgcaactg gtccagaacc ttgaccgaac gcagcggtgg taacggcgca   1740
gtggcggttt tcatggcttg ttatgactgt ttttttgggg tacagtctat gcctcgggca   1800
tccaagcagc aagcgcgtta cgccgtgggt cgatgtttga tgttatggag cagcaacgat   1860
gttacgcagc agggcagtcg ccctaaaaca aagttaaaca ttatgaggga agcggtgatc   1920
gccgaagtat cgactcaact atcagaggta gttggcgtca tcgagcgcca tctcgaaccg   1980
acgttgctgg ccgtacattt gtacggctcc gcagtggatg gcggcctgaa gccacacagt   2040
gatattgatt tgctggttac ggtgaccgta aggcttgatg aaacaacgcg gcgagctttg   2100
atcaacgacc ttttggaaac ttcggcttcc cctggagaga gcgagattct ccgcgctgta   2160
gaagtcacca ttgttgtgca cgacgacatc attccgtggc gttatccagc taagcgcgaa   2220
ctgcaatttg gagaatggca gcgcaatgac attcttgctg gtatcttcga gccagccacg   2280
atcgacattg atctggctat cttgctgaca aaagcaagag aacatagcgt tgccttggta   2340
ggtccagcgg cggaggaact ctttgatccg gttcctgaac aggatctatt tgaggcgcta   2400
```

```
aatgaaacct taacgctatg gaactcgccg cccgactggg ctggcgatga gcgaaatgta    2460
gtgcttacgt tgtcccgcat ttggtacagc gcagtaaccg gcaaaatcgc gccgaaggat    2520
gtcgctgccg actgggcaat ggagcgcctg ccggcccagt atcagcccgt catacttgaa    2580
gctagacagg cttatcttgg acaagaagaa gatcgcttgg cctcgcgcgc agatcagttg    2640
gaagaatttg tccactacgt gaaaggcgag atcaccaagg tagtcggcaa ataacctcat    2700
tttcgccaga tatcgacgtc gacatctcgc ttctgggctt caataaatgg ttccgattga    2760
tgataggttg attcatgagg aatctaaggc ttaattctcc acaaaagaat taagcgtccg    2820
tcgcaacgga atgctccgct ggacttgcgc tgtgggactg cagctttaca ggctccccct    2880
gccagaaatc ctgaatcgtc gagcatatct gacatatctc tagggagaga cgacgaattc    2940
aaaagatctt ttaagaagga gatatacata tgagtaaagg agaagaactt ttcactggag    3000
ttgtcccaat tcttgttgaa ttagatggtg atgttaatgg gcacaaattt tctgtcagtg    3060
gagagggtga aggtgatgca acatacggaa aacttaccct taaatttatt tgcactactg    3120
gaaaactacc tgttccgtgg ccaacacttg tcactacttt ctcttatggt gttcaatgct    3180
tttcccgtta tccggatcac atgaaacggc atgacttttt caagagtgcc atgcccgaag    3240
gttatgtaca ggaacgcact atatctttca agatgacgg gaactacaag acgcgtgctg    3300
aagtcaagtt tgaaggtgat acccttgtta atcgtatcga gttaaaaggt attgatttta    3360
aagaagatgg aaacattctc ggacacaaac tggagtacaa ctataactca cacaatgtat    3420
acatcacggc agacaaacaa aagaatggaa tcaaagctaa cttcaaaatt cgccacaaca    3480
ttgaagatgg ctccgttcaa ctagcagacc attatcaaca aaatactcca attggcgatg    3540
gccctgtcct tttaccagac aaccattacc tgtccacaca atctgccctt tcgaaagatc    3600
ccaacgaaaa gcgtgaccac atggtccttc ttgagtttgt aactgctgct gggattacac    3660
atggcatgga tgagctctac aaataaggat ccaaactcga gtaaggatct ccaggcatca    3720
aataaaacga aaggctcagt cgaaagactg ggcctttcgt tttatctgtt gtttgtcggt    3780
gaacgctctc tactagagtc acactggctc accttcgggt gggcctttct gcgtttatac    3840
ctagggcgtt cggctgcggc gagcggtatc agctcactca aaggcggtaa tacgtccctg    3900
ctcgtcacgc tttcaggcac cgtgccagat atcgacgtgg agtcgatcac tgtgattggc    3960
gaaggggaag gcagcgctac ccaaatcgct agcttgctgg agaagctgaa acaaaccacg    4020
ggcattgatc tggcgaaatc cctaccgggt caatccgact cgcccgctgc gaagtcctaa    4080
gagatagcga tgtgaccgcg atcgcttgtc aagaatccca gtgatcccga accataggaa    4140
ggcaagctca atgcttgcct cgtcttgagg actatctaga tgtctgtgga acgcacattt    4200
attgccatca agcccgatgg cgttcagcgg ggtttggtcg gtacgatcat cggccgcttt    4260
gagcaaaaag gcttcaaact ggtgggccta aagcagctga agcccagtcg cgagctggcc    4320
gaacagcact atgctgtcca ccgcgagcgc cccttcttca atggcctcgt cgagttcatc    4380
acctctgggc cgatcgtggc gatcgtcttg gaaggcgaag gcgttgtggc ggctgctcgc    4440
aagttgatcg gcgctaccaa tccgctgacg gcagaaccgg gcaccatccg tggtgatttt    4500
ggtgtcaata ttgccgcaa catcatccat ggctcggatg caatcgaaac agcacaacag    4560
gaaattgctc tctggtttag cccagcagag ctaagtgatt ggaccccac gattcaaccc    4620
tggctgtacg aataaggtct gcattccttc agagagacat tgccatgccc                4670

<210> SEQ ID NO 5
<211> LENGTH: 5195
```

```
<212> TYPE: DNA
<213> ORGANISM: Artificial Sequence
<220> FEATURE:
<223> OTHER INFORMATION: pSe1Bb2os-GFP vector
<220> FEATURE:
<221> NAME/KEY: rep_origin
<222> LOCATION: (58)..(673)
<223> OTHER INFORMATION: pUC origin
<220> FEATURE:
<221> NAME/KEY: unsure
<222> LOCATION: (745)..(1543)
<223> OTHER INFORMATION: NSIa
<220> FEATURE:
<221> NAME/KEY: gene
<222> LOCATION: (1684)..(2694)
<223> OTHER INFORMATION: Spectinomycin resistance gene
<220> FEATURE:
<221> NAME/KEY: gene
<222> LOCATION: (2721)..(3347)
<223> OTHER INFORMATION: tetR repressor
<220> FEATURE:
<221> NAME/KEY: promoter
<222> LOCATION: (3348)..(3459)
<223> OTHER INFORMATION: modified tet A promoter
<220> FEATURE:
<221> NAME/KEY: gene
<222> LOCATION: (3475)..(4211)
<223> OTHER INFORMATION: green fluorescent protein
<220> FEATURE:
<221> NAME/KEY: unsure
<222> LOCATION: (4420)..(5195)
<223> OTHER INFORMATION: NSIb

<400> SEQUENCE: 5
gataatctca tgaccaaaat cccttaacgt gagttttcgt tccactgagc gtcagacccc      60
gtagaaaaga tcaaaggatc ttcttgagat cctttttttc tgcgcgtaat ctgctgcttg     120
caaacaaaaa aaccaccgct accagcggtg gtttgtttgc cggatcaaga gctaccaact     180
ctttttccga aggtaactgg cttcagcaga gcgcagatac caaatactgt tcttctagtg     240
tagccgtagt taggccacca cttcaagaac tctgtagcac cgcctacata cctcgctctg     300
ctaatcctgt taccagtggc tgctgccagt ggcgataagt cgtgtcttac cgggttggac     360
tcaagacgat agttaccgga taaggcgcag cggtcgggct gaacggggg ttcgtgcaca      420 cagcccagct tggagcgaac gacctacacc gaactgagat acctacagcg tgagctatga     480
gaaagcgcca cgcttcccga agggagaaag gcggacaggt atccggtaag cggcagggtc     540
ggaacaggag agcgcacgag ggagcttcca gggggaaacg cctggtatct ttatagtcct     600
gtcgggtttc gccacctctg acttgagcgt cgatttttgt gatgctcgtc aggggggcgg     660
agcctatgga aaaacgccag caacgcggcc ttttttacggt tcctggcctt tgctggcct      720 tttgctcaca tgtgtgctgg gccccaatgc cttctccaag gcggcattc cctgactgt       780 tgaaggcgtt gccaatatca agattgctgg ggaagaaccg accatccaca acgcgatcga     840
gcggctgctt ggcaaaaacc gtaaggaaat cgagcaaatt gccaaggaga ccctcgaagg     900
caacttgcgt ggtgttttag ccagcctcac gccgagcag atcaacgagg acaaattgc       960 ctttgccaaa agtctgctgg aagaggcgga ggatgacctt gagcagctgg gtcaagtcct    1020
cgatacgctg caagtccaga acatttccga tgaggtcggt tatctctcgg ctagtggacg    1080
caagcagcgg gctgatctgc agcgagatgc ccgaattgct gaagccgatg cccaggctgc    1140
ctctgcgatc caaacggccg aaaatgacaa gatcacggcc ctgcgtcgga tcgatcgcga    1200
tgtagcgatc gcccaagccg aggccgagcg ccgattcag gatgcgttga cgcggcgcga     1260
agcggtggtg gccgaagctg aagcggacat tgctaccgaa gtcgctcgta gccaagcaga    1320
```

```
actccctgtg cagcaggagc ggatcaaaca ggtgcagcag caacttcaag ccgatgtgat    1380
cgccccagct gaggcagctt gtaaacgggc gatcgcggaa gcgcgggggg ccgccgcccg    1440
tatcgtcgaa gatggaaaag ctcaagcgga agggacccaa cggctggcgg aggcttggca    1500
gaccgctggt gctaatgccc gcgacatctt cctgctccag aagtctagac cagccaggac    1560
agaaatgcct cgacttcgct gctacccaag gttgccgggt gacgcacacc gtggaaacgg    1620
atgaaggcac gaacccagtg gacataagcc tgttcggttc gtaagctgta atgcaagtag    1680
cgtatgcgct cacgcaactg gtccagaacc ttgaccgaac gcagcggtgg taacggcgca    1740
gtggcggttt tcatggcttg ttatgactgt ttttttgggg tacagtctat gcctcgggca    1800
tccaagcagc aagcgcgtta cgccgtgggt cgatgtttga tgttatggag cagcaacgat    1860
gttacgcagc agggcagtcg ccctaaaaca aagttaaaca ttatgaggga agcggtgatc    1920
gccgaagtat cgactcaact atcagaggta gttggcgtca tcgagcgcca tctcgaaccg    1980
acgttgctgg ccgtacattt gtacggctcc gcagtggatg gcggcctgaa gccacacagt    2040
gatattgatt tgctggttac ggtgaccgta aggcttgatg aaacaacgcg gcgagctttg    2100
atcaacgacc ttttggaaac ttcggcttcc cctggagaga gcgagattct ccgcgctgta    2160
gaagtcacca ttgttgtgca cgacgacatc attccgtggc gttatccagc taagcgcgaa    2220
ctgcaatttg gagaatggca gcgcaatgac attcttgctg gtatcttcga ccagccacg    2280
atcgacattg atctggctat cttgctgaca aaagcaagag aacatagcgt tgccttggta    2340
ggtccagcgg cggaggaact ctttgatccg gttcctgaac aggatctatt tgaggcgcta    2400
aatgaaacct aacgctatg gaactcgccg cccgactggg ctggcgatga gcgaaatgta    2460
gtgcttacgt tgtcccgcat ttggtacagc gcagtaaccg gcaaaatcgc gccgaaggat    2520
gtcgctgccg actgggcaat ggagcgcctg ccggcccagt atcagcccgt catacttgaa    2580
gctagacagg cttatcttgg acaagaagaa gatcgcttgg cctcgcgcgc agatcagttg    2640
gaagaatttg tccactacgt gaaaggcgag atcaccaagg tagtcggcaa ataacctcat    2700
tttcgccaga tatcgacgtc ttaagaccca cttttcacatt taagttgttt ttctaatccg    2760
catatgatca attcaaggcc gaataagaag gctggctctg caccttggtg atcaaataat    2820
tcgatagctt gtcgtaataa tggcggcata ctatcagtag taggtgtttc ccttccttct    2880
ttagcgactt gatgctcttg atcttccaat acgcaaccta aagtaaaatg ccccacagcg    2940
ctgagtgcat ataatgcatt ctctagtgaa aaaccttgtt ggcataaaaa ggctaattga    3000
ttttcgagag tttcatactg ttttttctgta ggccgtgtac ctaaatgtac ttttgctcca    3060
tcgcgatgac ttagtaaagc acatctaaaa cttttagcgt tattacgtaa aaaatcttgc    3120
cagctttccc cttctaaagg gcaaaagtga gtatggtgcc tatctaacat ctcaatggct    3180
aaggcgtcga gcaaagcccg cttatttttt acatgccaat acaatgtagg ctgctctaca    3240
cctagcttct gggcgagttt acgggttgtt aaaccttcga ttccgacctc attaagcagc    3300
tctaatgcgc tgttaatcac tttacttta tctaatctag acatcattaa ttcctaattt    3360
ttgttgacac tctatcgttg atagagttat tttaccactc cctatcagtg atagagattg    3420
acatccctat cagtgataga gatataatgg ccactaaaag aattcaaaag atcttttaag    3480
aaggagatat acatatgagt aaaggagaag aacttttcac tggagttgtc ccaattcttg    3540
ttgaattaga tggtgatgtt aatgggcaca aattttctgt cagtggagag ggtgaaggtg    3600
atgcaacata cggaaaactt acccttaaat ttatttgcac tactggaaaa ctacctgttc    3660
cgtggccaac acttgtcact actttctctt atggtgttca atgcttttcc cgttatccgg    3720
```

| | |
|---|---|
| atcacatgaa acggcatgac tttttcaaga gtgccatgcc cgaaggttat gtacaggaac | 3780 |
| gcactatatc tttcaaagat gacgggaact acaagacgcg tgctgaagtc aagtttgaag | 3840 |
| gtgataccct tgttaatcgt atcgagttaa aaggtattga ttttaaagaa gatggaaaca | 3900 |
| ttctcggaca caaactggag tacaactata actcacacaa tgtatacatc acggcagaca | 3960 |
| aacaaaagaa tggaatcaaa gctaacttca aaattcgcca caacattgaa gatggctccg | 4020 |
| ttcaactagc agaccattat caacaaaata ctccaattgg cgatggccct gtccttttac | 4080 |
| cagacaacca ttacctgtcc acacaatctg ccctttcgaa agatcccaac gaaaagcgtg | 4140 |
| accacatggt ccttcttgag tttgtaactg ctgctgggat tacacatggc atggatgagc | 4200 |
| tctacaaata aggatccaaa ctcgagtaag gatctccagg catcaaataa acgaaaggc | 4260 |
| tcagtcgaaa gactgggcct ttcgttttat ctgttgtttg tcggtgaacg ctctctacta | 4320 |
| gagtcacact ggctcacctt cgggtgggcc tttctgcgtt tatacctagg cgttcggct | 4380 |
| gcggcgagcg gtatcagctc actcaaaggc ggtaatacgt ccctgctcgt cacgctttca | 4440 |
| ggcaccgtgc cagatatcga cgtggagtcg atcactgtga ttggcgaagg ggaaggcagc | 4500 |
| gctacccaaa tcgctagctt gctggagaag ctgaaacaaa ccacgggcat tgatctggcg | 4560 |
| aaatccctac cgggtcaatc cgactcgccc gctgcgaagt cctaagagat agcgatgtga | 4620 |
| ccgcgatcgc ttgtcaagaa tcccagtgat cccgaaccat aggaaggcaa gctcaatgct | 4680 |
| tgcctcgtct tgaggactat ctagatgtct gtggaacgca catttattgc catcaagccc | 4740 |
| gatggcgttc agcggggttt ggtcggtacg atcatcggcc gctttgagca aaaaggcttc | 4800 |
| aaactggtgg gcctaaagca gctgaagccc agtcgcgagc tggccgaaca gcactatgct | 4860 |
| gtccaccgcg agcgcccctt cttcaatggc ctcgtcgagt tcatcacctc tgggccgatc | 4920 |
| gtggcgatcg tcttggaagg cgaaggcgtt gtggcggctg ctcgcaagtt gatcggcgct | 4980 |
| accaatccgc tgacggcaga accgggcacc atccgtggtg attttggtgt caatattggc | 5040 |
| cgcaacatca tccatggctc ggatgcaatc gaaacagcac aacaggaaat tgctctctgg | 5100 |
| tttagcccag cagagctaag tgattggacc cccacgattc aaccctggct gtacgaataa | 5160 |
| ggtctgcatt ccttcagaga gacattgcca tgccc | 5195 |

<210> SEQ ID NO 6
<211> LENGTH: 112
<212> TYPE: DNA
<213> ORGANISM: Artificial Sequence
<220> FEATURE:
<223> OTHER INFORMATION: modified tet A promoter

<400> SEQUENCE: 6

| | |
|---|---|
| taattcctaa tttttgttga cactctatcg ttgatagagt tattttacca ctccctatca | 60 |
| gtgatagaga ttgacatccc tatcagtgat agagatataa tggccactaa aa | 112 |

<210> SEQ ID NO 7
<211> LENGTH: 799
<212> TYPE: DNA
<213> ORGANISM: Artificial Sequence
<220> FEATURE:
<223> OTHER INFORMATION: Neutral site 1a (NSIa)

<400> SEQUENCE: 7

| | |
|---|---|
| caatgccttc tccaagggcg gcattcccct gactgttgaa ggcgttgcca atatcaagat | 60 |
| tgctggggaa gaaccgacca tccacaacgc gatcgagcgg ctgcttggca aaaaccgtaa | 120 |

| | |
|---|---|
| ggaaatcgag caaattgcca aggagaccct cgaaggcaac ttgcgtggtg ttttagccag | 180 |
| cctcacgccg gagcagatca acgaggacaa aattgccttt gccaaaagtc tgctggaaga | 240 |
| ggcggaggat gaccttgagc agctgggtca agtcctcgat acgctgcaag tccagaacat | 300 |
| ttccgatgag gtcggttatc tctcggctag tggacgcaag cagcgggctg atctgcagcg | 360 |
| agatgcccga attgctgaag ccgatgccca ggctgcctct cgcatccaaa cggccgaaaa | 420 |
| tgacaagatc acggccctgc gtcggatcga tcgcgatgta gcgatcgccc aagccgaggc | 480 |
| cgagcgccgg attcaggatg cgttgacgcg gcgcgaagcg gtggtggccg aagctgaagc | 540 |
| ggacattgct accgaagtcg ctcgtagcca agcagaactc cctgtgcagc aggagcggat | 600 |
| caaacaggtg cagcagcaac ttcaagccga tgtgatcgcc ccagctgagg cagcttgtaa | 660 |
| acgggcgatc gcggaagcgc gggggggccgc cgcccgtatc gtcgaagatg aaaagctca | 720 |
| agcggaaggg acccaacggc tggcggaggc ttggcagacc gctggtgcta atgcccgcga | 780 |
| catcttcctg ctccagaag | 799 |

<210> SEQ ID NO 8
<211> LENGTH: 776
<212> TYPE: DNA
<213> ORGANISM: Artificial Sequence
<220> FEATURE:
<223> OTHER INFORMATION: Neutral site 1b (NS1b)

<400> SEQUENCE: 8

| | |
|---|---|
| tccctgctcg tcacgctttc aggcaccgtg ccagatatcg acgtggagtc gatcactgtg | 60 |
| attggcgaag gggaaggcag cgctacccaa atcgctagct tgctggagaa gctgaaacaa | 120 |
| accacgggca ttgatctggc gaaatcccta ccgggtcaat ccgactcgcc cgctgcgaag | 180 |
| tcctaagaga tagcgatgtg accgcgatcg cttgtcaaga atcccagtga tcccgaacca | 240 |
| taggaaggca agctcaatgc ttgcctcgtc ttgaggacta tctagatgtc tgtggaacgc | 300 |
| acatttattg ccatcaagcc cgatggcgtt cagcggggtt tggtcggtac gatcatcggc | 360 |
| cgctttgagc aaaaaggctt caaactggtg ggcctaaagc agctgaagcc cagtcgcgag | 420 |
| ctggccgaac agcactatgc tgtccaccgc gagcgcccct tcttcaatgg cctcgtcgag | 480 |
| ttcatcacct ctgggccgat cgtggcgatc gtcttggaag gcgaaggcgt tgtggcggct | 540 |
| gctcgcaagt tgatcggcgc taccaatccg ctgacggcag aaccgggcac catccgtggt | 600 |
| gattttggtg tcaatattgg ccgcaacatc atccatggct cggatgcaat cgaaacagca | 660 |
| caacaggaaa ttgctctctg gtttagccca gcagagctaa gtgattggac ccccacgatt | 720 |
| caaccctggc tgtacgaata aggtctgcat tccttcagag agacattgcc atgccc | 776 |

<210> SEQ ID NO 9
<211> LENGTH: 22
<212> TYPE: DNA
<213> ORGANISM: Artificial Sequence
<220> FEATURE:
<223> OTHER INFORMATION: primer

<400> SEQUENCE: 9

| | |
|---|---|
| aaagacgtca tctcgcttct gg | 22 |

```
<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10
tttgaattcg tcgtctctcc ct                                              22
```